United States Patent
Belmont et al.

(10) Patent No.: US 9,035,072 B2
(45) Date of Patent: May 19, 2015

(54) PROCESS OF PRODUCING CYCLOALKYLCARBOXAMIDO-INDOLE COMPOUNDS

(75) Inventors: Daniel T. Belmont, Grafton, MA (US); Cristian Harrison, Beveryly, MA (US); Robert Michael Hughes, San Diego, CA (US); Young Chun Jung, Lexington, MA (US); Elaine Chungmin Lee, Arlington, MA (US); Benjamin Joseph Littler, Carlsbad, CA (US); Peter Jamison Rose, Littleton, MA (US); David Andrew Siesel, San Diego, CA (US); Gerald J. Tanoury, Marlborough, MA (US)

(73) Assignee: Vertex Pharmaceuticals Incorporated, Boston, MA (US)

(*) Notice: Subject to any disclaimer, the term of this patent is extended or adjusted under 35 U.S.C. 154(b) by 246 days.

(21) Appl. No.: 13/642,642

(22) PCT Filed: Apr. 21, 2011

(86) PCT No.: PCT/US2011/033396
§ 371 (c)(1),
(2), (4) Date: Aug. 14, 2013

(87) PCT Pub. No.: WO2011/133751
PCT Pub. Date: Oct. 27, 2011

(65) Prior Publication Data
US 2013/0324743 A1 Dec. 5, 2013

Related U.S. Application Data

(60) Provisional application No. 61/333,870, filed on May 12, 2010, provisional application No. 61/329,510, filed on Apr. 29, 2010, provisional application No. 61/329,500, filed on Apr. 29, 2010, provisional application No. 61/329,493, filed on Apr. 29, 2010, provisional application No. 61/327,095, filed on Apr. 22, 2010, provisional application No. 61/327,091, filed on Apr. 22, 2010, provisional application No. 61/327,057, filed on Apr. 22, 2010, provisional application No. 61/327,099, filed on Apr. 22, 2010.

(51) Int. Cl.
*C07D 209/40* (2006.01)
*C07D 405/12* (2006.01)
*C07D 209/12* (2006.01)
*C07D 317/46* (2006.01)
*C07D 317/60* (2006.01)

(52) U.S. Cl.
CPC ............ *C07D 405/12* (2013.01); *C07D 209/12* (2013.01); *C07D 317/46* (2013.01); *C07D 317/60* (2013.01)

(58) Field of Classification Search
CPC ..................................................... C07D 209/40
USPC ........................................................ 548/454
See application file for complete search history.

(56) References Cited

U.S. PATENT DOCUMENTS

2009/0131492 A1 5/2009 Ruah et al.
2011/0098484 A1 4/2011 Saitoh et al.

FOREIGN PATENT DOCUMENTS

| CN | 101151257 | 3/2008 |
|---|---|---|
| CN | 101460489 | 6/2009 |
| EP | 1864978 | 12/2007 |
| WO | WO 0211883 | 2/2002 |
| WO | WO 0212236 | 2/2002 |
| WO | WO 2007117715 | 10/2007 |

OTHER PUBLICATIONS

Miyamatsu et al. Journal of Medicinal Chemistry (1974), vol. 17 (5), 491-496.*
Beare, Neil, A., et al. "Palladium-Catalyzed Arylation of Malonates and Cyanoesters Using Sterically Hindered Trialkyl- and Ferrocenyldialkylphosphine Ligands", Journal of Organic Chemistry, American Chemical Society, Easton.; US., vol. 67 (Jan. 1, 2002), pp. 541-555.
Stauffer, Shaun, R., et al., "Palladium-Catalyzed Arylation of Ethyl Cyanoacetate. Fluorescence Resonance Energy Transfer as a Tool for Reaction Discovery", Journal of the Americal Chemical Society, American Chemical Society, Washington, D.C.; US, vol. 123, No. 19 (Jan. 1, 2001), pp. 4641-4642.
Suzuki, Hitomi, et al., "A Simple One-Pot Conversion of Aryl Halides into Arylacetonitriles", The Chemical Society of Japan, Chemistry Letters, 1983, pp. 193-194.
PCT/US2011/033396 International Search Report, mailed Nov. 11, 2011.

* cited by examiner

*Primary Examiner* — Nyeemah A Grazier
(74) *Attorney, Agent, or Firm* — Honigman Miller Schwartz and Cohn LLP; Heidi M. Berven; Jonathan P. O'Brien

(57) ABSTRACT

The present invention features processes for preparing compounds, such as (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide (Compound 1), useful for treating CFTR mediated diseases such as cystic fibrosis.

26 Claims, No Drawings

PROCESS OF PRODUCING CYCLOALKYLCARBOXAMIDO-INDOLE COMPOUNDS

CROSS REFERENCE TO RELATED APPLICATIONS

This application is a U.S. National Phase filing of PCT Application No.: PCT/US2011/33396, filed Apr. 21, 2011, which claims priority to U.S. provisional patent application Ser. No. 61/333,870, filed May 12, 2010; 61/327,095, filed Apr. 22, 2010; 61/327,057, filed Apr. 22, 2010; 61/329,493, filed Apr. 29, 2010; 61/327,091, filed Apr. 22, 2010; 61/329,510, filed Apr. 29, 2010; 61/327,099, filed Apr. 22, 2010; and 61/329,500, filed Apr. 29, 2010, the entire contents of all applications are incorporated herein by reference.

TECHNICAL FIELD OF THE INVENTION

The present invention features processes for preparing compounds useful for treating CFTR mediated diseases such as cystic fibrosis.

BACKGROUND OF THE INVENTION

CFTR is a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, >1000 disease causing mutations in the CF gene have been identified (www.genet.sicld-cids.on.ca/cftr/). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease. Other mutations include the R117H and G551D.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$-$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$-$K^+$-ATPase pump and Cl-channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$-$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. Infact, this cellular phenomenon of defective ER processing of ABC transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)].

(R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide is disclosed in US published patent application US20090131492 (said publication being incorporated herein by reference in its entirety) as a modulator of CFTR activity and thus useful in treating CFTR-mediated diseases such as cystic fibrosis. There remains, however, a need for economical processes for the preparation of the cycloalkylcarboxamido-indole compounds described herein.

SUMMARY OF THE INVENTION

As described herein, the present invention provides processes for preparing CFTR correctors useful in the treatment of CFTR mediated diseases, such as cystic fibrosis. Such compounds include (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (hereinafter "Compound 1") which has the structure below:

Compound 1

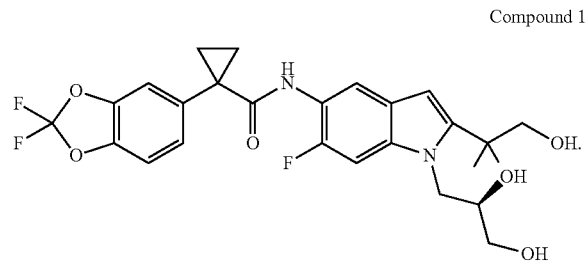 [SMILES: CC(C)(CO)c1cc2cc(NC(=O)C3(c4ccc5c(c4)OC(F)(F)O5)CC3)c(F)cc2n1C[C@@H](O)CO]

Compound 1 and pharmaceutically acceptable compositions thereof are useful for treating or lessening the severity of CFTR mediated diseases such as, for example, cystic fibrosis. Compound 1 may exist in several different solid forms such as substantially crystalline forms or amorphous forms.

DETAILED DESCRIPTION OF THE INVENTION

Definitions

As used herein, the following definitions shall apply unless otherwise indicated.

The term "CFTR" as used herein means cystic fibrosis transmembrane conductance regulator or a mutation thereof capable of regulator activity, including, but not limited to, ΔF508 CFTR and G551D CFTR (see, e.g., www.genet.sickkids.on.ca/cftr/, for CFTR mutations).

The term "modulating" as used herein means increasing or decreasing, e.g. activity, by a measurable amount.

The term "chemically stable", as used herein, means that the solid form of Compound 1 does not decompose into one or more different chemical compounds when subjected to specified conditions, e.g., 40° C./75% relative humidity, for a specific period of time. e.g. 1 day, 2 days, 3 days, 1 week, 2 weeks, or longer. In some embodiments, less than 25% of the solid form of Compound 1 decomposes, in some embodiments, less than about 20%, less than about 15%, less than about 10%, less than about 5%, less than about 3%, less than about 1%, less than about 0.5% of the form of Compound 1 decomposes under the conditions specified. In some embodiments, no detectable amount of the solid form of Compound 1 decomposes.

The term "physically stable", as used herein, means that the solid form of Compound 1 does not change into one or more different physical forms of Compound 1 (e.g. different solid forms as measured by XRPD, DSC, etc.) when subjected to specific conditions, e.g., 40° C./75% relative humidity, for a specific period of time. e.g. 1 day, 2 days, 3 days, 1 week, 2 weeks, or longer. In some embodiments, less than 25% of the solid form of Compound 1 changes into one or more different physical forms when subjected to specified conditions. In some embodiments, less than about 20%, less than about 15%, less than about 10%, less than about 5%, less than about 3%, less than about 1%, less than about 0.5% of the solid form of Compound 1 changes into one or more different physical forms of Compound 1 when subjected to specified conditions. In some embodiments, no detectable amount of the solid form of Compound 1 changes into one or more physically different solid forms of Compound 1.

As used herein, the terms "about" and "approximately", when used in connection with doses, amounts, or weight percent of ingredients of a composition or a dosage form, mean a dose, amount, or weight percent that is recognized by one of ordinary skill in the art to provide a pharmacological effect equivalent to that obtained from the specified dose, amount, or weight percent. Specifically the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. All tautomeric forms of the Compound 1 are included herein. For example, Compound 1 may exist as tautomers, both of which are included herein:

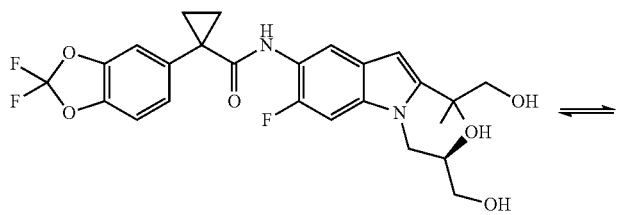 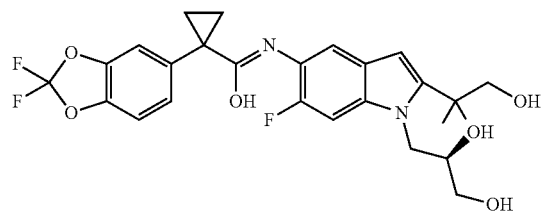

Additionally, unless otherwise stated, structures depicted herein are also meant to include compounds that differ only in the presence of one or more isotopically enriched atoms. For example, Compound 1, wherein one or more hydrogen atoms are replaced deuterium or tritium, or one or more carbon atoms are replaced by a $^{13}C$—or $^{14}C$-enriched carbon are within the scope of this invention. Such compounds are useful, for example, as analytical tools, probes in biological assays, or compounds with improved therapeutic profile.

The term "protecting group," abbreviated as P, as used herein refers to any chemical group introduced into a molecule by chemical modification of a functional group in order to obtain chemoselectivity in a subsequent chemical reaction. Non-limiting examples of alcohol protecting groups include acetyl (Ac), benzoyl (Bz), benzyl (Bn), β-methoxyethoxymethyl ether (MEM), dimethoxytrityl (DMT), methoxymethyl ether (MOM), methoxytrityl (MMT), p-methoxybenzyl ether (PMB), pivaloyl (Piv), tetrahydropyranyl (THP), trityl (Tr), and trimethylsilyl (TMS). In one embodiment, the protecting group is Bn which has the structure $-CH_2C_6H_5$.

The abbreviation "DCM" stands for dichloromethane. The abbreviation "IPA" stands for isopropyl alcohol. The abbreviation "DMSO" stands for dimethylsulfoxide. The abbreviation "MTBE" stands for methyl t-butyl ether. The abbreviation "THF" stands for tetrahydrofuran. The abbreviation "TEA" stands for triethylamine. The abbreviation "dba" as in $Pd(dba)_2$ stands for dibenzylideneacetone. The abbreviation "dppf" as in $Pd(dppf)Cl_2$ stands for stands for 1,1'-bis(diphenylphosphino) ferrocene.

In one aspect, the invention features a method for preparing a compound of formula I:

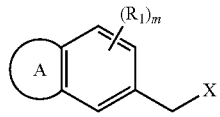
I wherein, independently for each occurrence:
ring A is a fused cycloalkyl, heterocycloalkyl, aryl, or heteroaryl ring;
$R_1$ is independently selected from $-R^J$, $-OR^J$, $-N(R^J)_2$, $-NO_2$, halogen, $-CN$, $-C_{1-4}$haloalkyl, $-C_{1-4}$haloalkoxy, $-C(O)N(R^J)_2$, $-NR^JC(O)R^J$, $-SOR^J$, $-SO_2R^J$, $-SO_2N(R^J)_2$, $-NR^JSO_2R^J$, $-COR^J$, $-CO_2R^J$, $-NR^JSO_2N(R^J)_2$, $-COCOR^J$;
$R^J$ is hydrogen or $C_{1-6}$ aliphatic;
X is CN or $CO_2R$;
R is $C_{1-6}$ aliphatic or aryl; and
m is an integer from 0 to 3 inclusive;
comprising the steps of
a) reacting a compound of formula IA in a first organic solvent

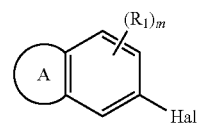
IA wherein, independently for each occurrence:
ring A is a fused cycloalkyl, heterocycloalkyl, aryl, or heteroaryl ring;
$R_1$ is independently selected from $-R^J$, $-OR^J$, $-N(R^J)_2$, $-NO_2$, halogen, $-CN$, $-C_{1-4}$haloalkyl, $-C_{1-4}$haloalkoxy, $-C(O)N(R^J)_2$, $-NR^JC(O)R^J$, $-SOR^J$, $-SO_2R^J$, $-SO_2N(R^J)_2$, $-NR^JSO_2R^J$, $-COR^J$, $-CO_2R^J$, $-NR^JSO_2N(R^J)_2$, $-COCOR^J$;
$R^J$ is hydrogen or $C_{1-6}$ aliphatic;
m is an integer from 0 to 3 inclusive; and
Hal is a halide;
with a compound of formula IB:

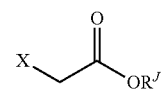
IB wherein $R^J$ is hydrogen or $C_{1-6}$ aliphatic, to form a compound of formula IC:

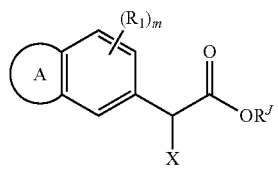
IC wherein, independently for each occurrence:
ring A is a fused cycloalkyl, heterocycloalkyl, aryl, or heteroaryl ring;
$R_1$ is independently selected from $-R^J$, $-OR^J$, $-N(R^J)_2$, $-NO_2$, halogen, $-CN$, $-C_{1-4}$haloalkyl, $-C_{1-4}$haloalkoxy, $-C(O)N(R^J)_2$, $-NR^JC(O)R^J$, $-SOR^J$, $-SO_2R^J$, $-SO_2N(R^J)_2$, $-NR^JSO_2R^J$, $-COR^J$, $-CO_2R^J$, $-NR^JSO_2N(R^J)_2$, $-COCOR^J$;
$R^J$ is hydrogen or $C_{1-6}$ aliphatic;
X is CN or $CO_2R$;
R is R is $C_{1-6}$ aliphatic or aryl; and
m is an integer from 0 to 3 inclusive; and
b) removing the $-CO_2R^J$ group from compound IC in a second organic solvent to form a compound of formula I.

In another embodiment, the invention features the above method wherein ring A is a fused heterocycloalkyl or heteroaryl. In another embodiment, ring A is selected from

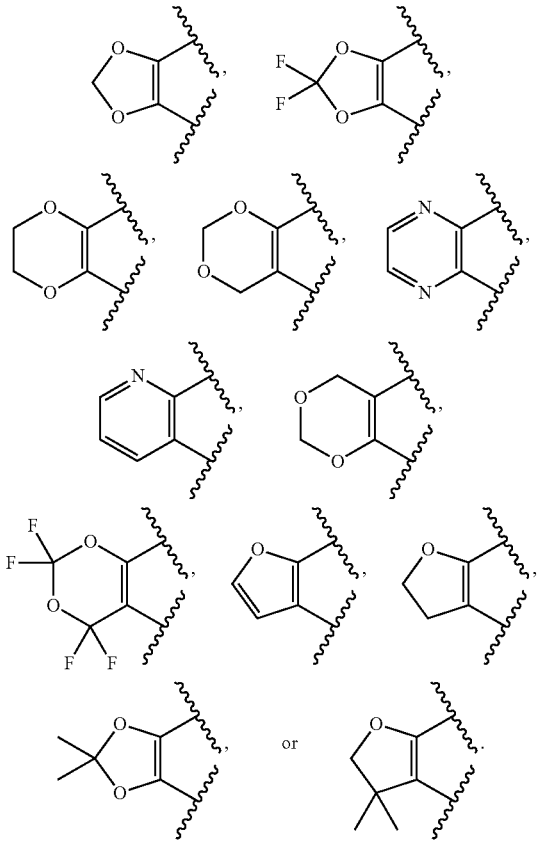

In another embodiment, ring A is S

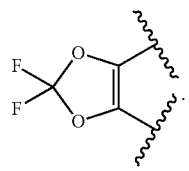 [SMILES: *C1=C(*)OC(F)(F)O1]

In another embodiment, the invention features the above method wherein X is CN. In another embodiment, X is $CO_2Et$.

In another embodiment, the invention features the above method wherein m is 0.

In another embodiment, the invention features the above method wherein $R^J$ is a $C_{1-6}$ aliphatic. In another embodiment, $R^J$ is —$CH_2CH_3$.

In another embodiment, the invention features the above method wherein Hal is Br.

In another embodiment, the invention features the above method wherein the first organic solvent is an aprotic solvent. In another embodiment, the first organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, the first organic solvent is selected from acetonitrile, toluene, benzene, or xylenes. In another embodiment, the first organic solvent is toluene.

In another embodiment, the invention features the above method wherein step a) is carried out in the presence of a transition metal catalyst. In another embodiment, step a) is carried out in the presence of a palladium catalyst. In another embodiment, step a) is carried out in the presence of a palladium catalyst selected from palladium(II)acetate, Pd(dppf)$Cl_2$, Pd(dba)$_2$, tetrakis(triphenylphosphine)palladium(0) or tris(dibenzylideneacetone)dipalladium(0). In another embodiment, step a) is carried out in the presence of Pd(dba)$_2$.

In another embodiment, the invention features the above method wherein step a) is carried out at about 50° C. to 90° C. In another embodiment, step a) is carried out at about 60° C. to 80° C. In another embodiment, step a) is carried out at about 70° C.

In another embodiment, the invention features the above method wherein the second organic solvent is an aprotic solvent. In another embodiment, the second organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, the second organic solvent is dimethylsulfoxide.

In another embodiment, the invention features the above method wherein step b) is carried out in the presence of an inorganic acid. In another embodiment, step b) is carried out in the presence of an inorganic acid selected from hydrochloric, sulfuric, nitric, phosphoric, or boric acid. In another embodiment, step b) is carried out in the presence of hydrochloric acid.

In another embodiment, the invention features the above method wherein step b) is carried out at about 55° C. to 95° C. In another embodiment, step b) is carried out at about 65° C. to 85° C. In another embodiment, step b) is carried out at about 75° C.

In another aspect, the invention features a method for preparing a compound of formula II:

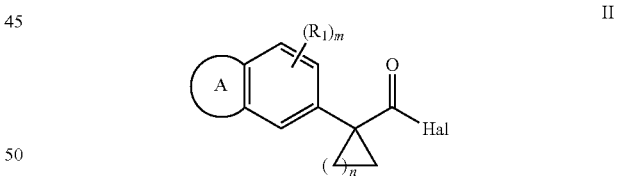

wherein, independently for each occurrence:
ring A is a fused cycloalkyl, heterocycloalkyl, aryl, or heteroaryl ring;
Hal is a halide;
$R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —C(O)N($R^J$)$_2$, —$NR^J$C(O)$R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
$R^J$ is hydrogen or $C_{1-6}$ aliphatic;
m is an integer from 0 to 3 inclusive; and
n is an integer from 1 to 4 inclusive;
comprising the steps of
a) reacting a compound of formula IIA in a first organic solvent

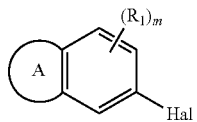

IIA wherein, independently for each occurrence:
ring A is a fused cycloalkyl, heterocycloalkyl, aryl, or heteroaryl ring;
$R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
$R^J$ is hydrogen or $C_{1-6}$ aliphatic;
m is an integer from 0 to 3 inclusive; and
Hal is a halide;
with a compound of formula IIB:

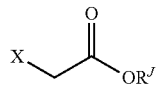

IIB wherein
X is CN or $CO_2R$;
R is $C_{1-6}$ aliphatic or aryl; and
$R^J$ is hydrogen or $C_{1-6}$ aliphatic, to form a compound of formula IIC:

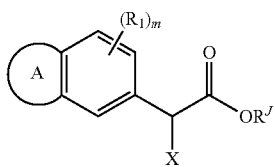

IIC wherein, independently for each occurrence:
ring A is a fused cycloalkyl, heterocycloalkyl, aryl, or heteroaryl ring;
$R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R_J)_2$, —$NR^JSO_2R^J$, —$COR^J$, —$CO_2R^J$, —$NR^JSO_2N(R^J)_2$, —$COCOR^J$;
$R^J$ is hydrogen or $C_{1-6}$ aliphatic;
X is CN or $CO_2R$;
R is $C_{1-6}$ aliphatic or aryl; and
m is an integer from 0 to 3 inclusive;
b) removing the —$CO_2R^J$ group from compound IIC in a second organic solvent to form a compound of formula I:

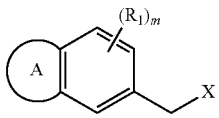

I wherein, independently for each occurrence:
ring A is a fused cycloalkyl, heterocycloalkyl, aryl, or heteroaryl ring;
$R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
$R^J$ is hydrogen or $C_{1-6}$ aliphatic;
X is CN or $CO_2R$;
R is $C_{1-6}$ aliphatic or aryl; and
m is an integer from 0 to 3 inclusive;
c) reacting a compound of formula I with a compound of formula IID in the presence of a base:

IID wherein, independently for each occurrence:
Hal is a halide; and
q is an integer from 0 to 3 inclusive; to produce a compound of formula IIE:

IIE wherein, independently for each occurrence:
ring A is a fused cycloalkyl, heterocycloalkyl, aryl, or heteroaryl ring;
$R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
$R^J$ is hydrogen or $C_{1-6}$ aliphatic;
m is an integer from 0 to 3 inclusive;
X is CN or $CO_2R$;
R is $C_{1-6}$ aliphatic or aryl; and
n is an integer from 1 to 4 inclusive;
d) sequentially reacting a compound of formula IIE with a hydroxide base and acid to form a compound of formula IIF:

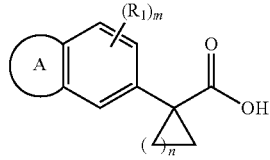

IIF wherein, independently for each occurrence:
ring A is a fused cycloalkyl, heterocycloalkyl, aryl, or heteroaryl ring;
$R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;

R$^J$ is hydrogen or C$_{1-6}$ aliphatic;

m is an integer from 0 to 3 inclusive; and n is an integer from 1 to 4 inclusive; and e) reacting a compound of formula IIF with a halogenating agent in a third organic solvent to form a compound of formula II.

In another embodiment, the invention features the above method wherein in step a), the first organic solvent is an aprotic solvent. In another embodiment, the first organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, the first organic solvent is toluene.

In another embodiment, the invention features the above method wherein in step a), m is 0.

In another embodiment, the invention features the above method wherein in step a), Hal is Br.

In another embodiment, the invention features the above method wherein in step a), ring A is a fused heterocyclic or heteroaryl ring. In another embodiment, ring A is selected from

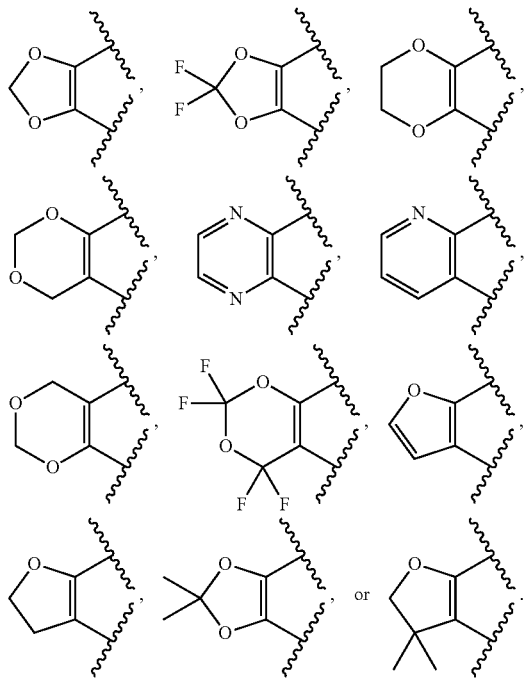

In another embodiment, ring A is

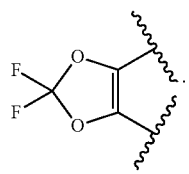

In another embodiment, the invention features the above method wherein in step a), X is CN. In another embodiment, X is CO$_2$Et.

In another embodiment, the invention features the above method wherein in step a) R$^J$ is Et.

In another embodiment, the invention features the above method wherein in formula IIC, ring A is

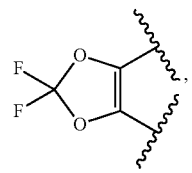

m is 0, X is CN, and R$^J$ is Et.

In another embodiment, the invention features the above method wherein in step b), the second solvent is an aprotic solvent. In another embodiment, the second solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, the second solvent is dimethylsulfoxide.

In another embodiment, the invention features the above method wherein in formula I, ring A is

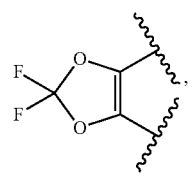

m is 0, and X is CN.

In another embodiment, the invention features the above method wherein in step c), the base is an inorganic base. In another embodiment, the base is a hydroxide. In another embodiment, the base is NaOH.

In another embodiment, the invention features the above method wherein in formula IID, q is 1.

In another embodiment, the invention features the above method wherein in formula IID, one Hal is Cl and the other Hal is Br.

In another embodiment, the invention features the above method wherein in step d), the base is NaOH. In another embodiment, in step d), the acid is HCl.

In another embodiment, the invention features the above method wherein in step d), reaction with a hydroxide base takes place at about 60° C. to 100° C. In another embodiment, reaction with a hydroxide takes place at about 70° C. to 90° C. In another embodiment, reaction with a hydroxide takes place at about 80° C.

In another embodiment, the invention features the above method wherein in formula IIE, ring A is

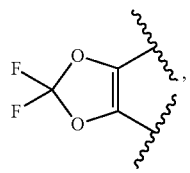

m is 0, n is 1, and X is CN.

In another embodiment, the invention features the above method wherein in step e), the third organic solvent is an aprotic solvent. In another embodiment, in step e), the third organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, in step e), the third organic solvent is toluene.

In another embodiment, the invention features the above method wherein in step e), the halogenating agent is $SOCl_2$.

In another embodiment, the invention features the above method wherein step e) takes place at about 40° C. to 80° C. In another embodiment, step e) takes place at about 50° C. to 70° C. In another embodiment, step e) takes place at about 60° C.

In another embodiment, the invention features the above method wherein in formula IIF, ring A is

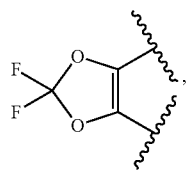

m is 0, and n is 1.

In another embodiment, the invention features the above method wherein in formula II, ring A is

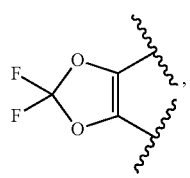

m is 0, n is 1, and Hal is Cl.

In another aspect, the invention features a method of preparing a compound of formula III:

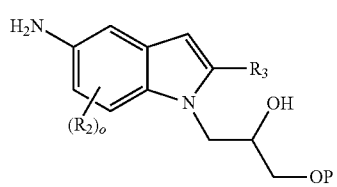

III wherein, independently for each occurrence:
  $R_2$ is —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
  $R^J$ is hydrogen or $C_{1-6}$ aliphatic;
  $R_3$ is $C_{1-6}$ aliphatic optionally substituted with OH, OP, —O—$C_{1-6}$ aliphatic, aryl, heteroaryl, —O-aryl, or —O-heteroaryl;
  P is a protecting group; and
  o is an integer from 0 to 3;
comprising the steps of:
  a) reacting a compound of formula IIIA:

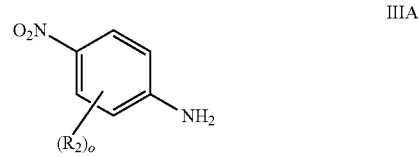

IIIA wherein, independently for each occurrence:
  $R_2$ is —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
  $R^J$ is hydrogen or $C_{1-6}$ aliphatic; and
  o is an integer from 0 to 3;
with a halogenating reagent in a first organic solvent to form a compound of formula IIIB:

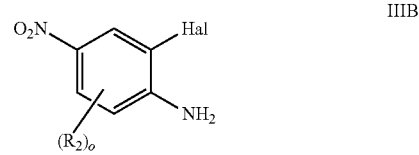

IIIB wherein, independently for each occurrence:
  $R_2$ is —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
  $R^J$ is hydrogen or $C_{1-6}$ aliphatic;
  o is an integer from 0 to 3; and
  Hal is a halide;
  b) reacting the compound of formula IIIB in a second organic solvent with a compound of formula IIIC:

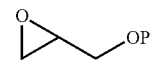

IIIC wherein:
  P is a protecting group;
followed by reduction and treatment with acid to form a compound of formula IIID:

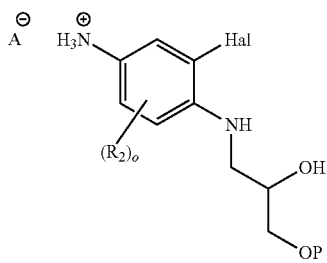
IIID wherein:
$R_2$ is —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
$R^J$ is hydrogen or $C_{1-6}$ aliphatic;
o is an integer from 0 to 3;
Hal is a halide;
P is a protecting group; and
$A^\ominus$ is an anion;
c) neutralizing a compound of formula IIID in the presence of a base to form a compound of formula IIID-a:

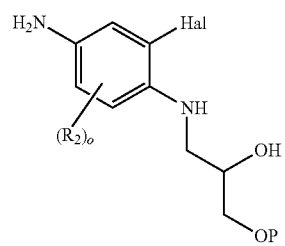
IIID-a wherein:
$R_2$ is —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
$R^J$ is hydrogen or $C_{1-6}$ aliphatic;
o is an integer from 0 to 3;
Hal is a halide; and
P is a protecting group;
d) reacting a compound of formula IIID-a in a third organic solvent with a compound of formula IIIE:

IIIE wherein, independently for each occurrence:
$R_3$ is a $C_{1-6}$ aliphatic optionally substituted with OH, OP, —O—$C_{1-6}$ aliphatic, aryl, heteroaryl, —O-aryl, or —O-heteroaryl;
in the presence of a catalyst to form a compound of formula III.

In another embodiment, the invention features the above method wherein in formula IIIA, o is 1. In another embodiment, o is 1 and $R_2$ is F.

In another embodiment, the invention features the above method wherein in step a), the halogenating reagent is N-bromosuccinimide.

In another embodiment, the invention features the above method wherein in step a), the first organic solvent is an aprotic solvent. In another embodiment, the first organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, the first organic solvent is ethyl acetate.

In another embodiment, the invention features the above method wherein step a) takes place at about 2° C. to 42° C. In another embodiment, step a) takes place at about 12° C. to 32° C. In another embodiment, step a) takes place at about 22° C.

In another embodiment, the invention features the above method wherein in formula IIIB, o is 1, $R_2$ is F, and Hal is Br.

In another embodiment, the invention features the above method wherein in formula IIIC, P is benzyl.

In another embodiment, the invention features the above method wherein in step b), the second organic solvent is an aprotic solvent. In another embodiment, in step b), the second organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, in step b), the second organic solvent is toluene.

In another embodiment, the invention features the above method wherein in step b), the reaction with a compound of formula IIIC takes place at about 60° C. to 100° C. In another embodiment, in step b), the reaction with a compound of formula IIIC takes place at about 70° C. to 90° C. In another embodiment, in step b), the reaction with a compound of formula IIIC takes place at about 80° C.

In another embodiment, the invention features the above method wherein in step b), reduction is carried out with hydrogen.

In another embodiment, the invention features the above method wherein in step b), the acid is p-toluenesulfonic acid.

In another embodiment, the invention features the above method wherein in formula IIID, o is 1, $R_2$ is F, Hal is Br, $A^-$ is Tos$^-$, and P is benzyl.

In another embodiment, the invention features the above method wherein in formula IIIE, $R_3$ is $C(CH_3)_2CH_2O$(benzyl).

In another embodiment, the invention features the above method wherein in step c), the base is an inorganic base.

In another embodiment, the invention features the above method wherein in step c), the base is $NaHCO_3$.

In another embodiment, the invention features the above method wherein in step d), the third organic solvent is an aprotic solvent. In another embodiment, in step d), the third organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, in step d), the third organic solvent is acetonitrile.

In another embodiment, the invention features the above method wherein step d) takes place at about 60° C. to 100° C.

In another embodiment, step d) takes place at about 70° C. to 90° C. In another embodiment, step d) takes place at about 80° C.

In another embodiment, the invention features the above method wherein in step d), the catalyst is a palladium catalyst. In another embodiment, in step d), the catalyst is selected from palladium(II)acetate, Pd(dppf)Cl$_2$, Pd(dba)$_2$, (MeCN)$_2$PdCl$_2$, tetrakis(triphenylphosphine)palladium(0) or tris(dibenzylideneacetone)dipalladium(0). In another embodiment, in step d), the catalyst is palladium(II)acetate.

In another aspect, the invention features a method of preparing a compound of formula IV:

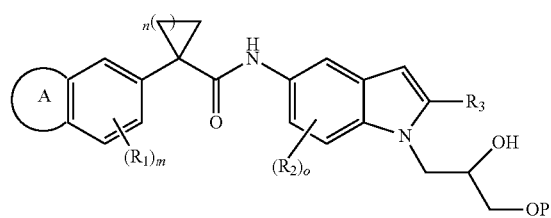

IV wherein, independently for each occurrence:
  ring A is a fused cycloalkyl, heterocycloalkyl, aryl, or heteroaryl ring;
  $R_1$ and $R_2$ is independently selected from —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;
  R$^J$ is hydrogen or C$_{1-6}$ aliphatic;
  $R_3$ is a C$_{1-6}$ aliphatic optionally substituted with OH, OP, —O—C$_{1-6}$ aliphatic, aryl, heteroaryl, —O-aryl, or —O-heteroaryl;
  P is a protecting group;
  m is an integer from 0 to 3 inclusive;
  n is an integer from 1 to 4 inclusive; and
  o is an integer from 1 to 3 inclusive;
comprising the steps of:
  a) reacting a compound of formula IIIA:

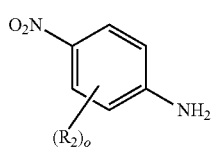

IIIA wherein, independently for each occurrence:
  $R_2$ is —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;
  R$^J$ is hydrogen or C$_{1-6}$ aliphatic; and
  o is an integer from 0 to 3;
with a halogenating reagent in a first organic solvent to form a compound of formula IIIB:

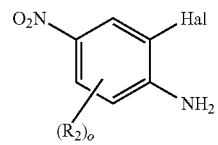

IIIB wherein, independently for each occurrence:
  $R_2$ is —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;
  R$^J$ is hydrogen or C$_{1-6}$ aliphatic;
  o is an integer from 0 to 3; and
  Hal is a halide;
  b) reacting the compound of formula IIIB in a second organic solvent with a compound of formula IIIC:

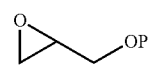

IIIC wherein:
  P is a protecting group;
followed by reduction and treatment with acid to form a compound of formula IIID:

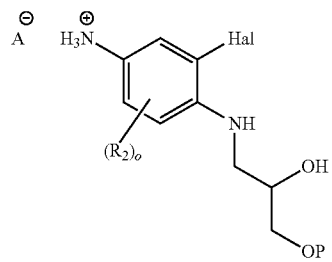

IIID wherein:
  $R_2$ is —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;
  R$^J$ is hydrogen or C$_{1-6}$ aliphatic;
  o is an integer from 0 to 3;
  Hal is a halide;
  P is a protecting group; and
  A$^⊖$ is an anion;
  c) neutralizing a compound of formula IIID in the presence of a base to form a compound of formula IIID-a:

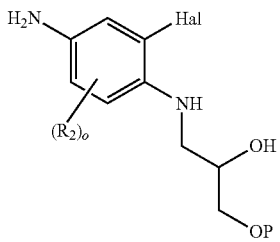

IIID-a wherein:
- $R_2$ is —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
- $R^J$ is hydrogen or $C_{1-6}$ aliphatic;
- o is an integer from 0 to 3;
- Hal is a halide; and
- P is a protecting group;

d) reacting a compound of formula IIID in a third organic solvent with a compound of formula IIIE:

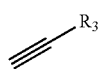

IIIE wherein, independently for each occurrence:
- $R_3$ is a $C_{1-6}$ aliphatic optionally substituted with OH, OP, —O—$C_{1-6}$ aliphatic, aryl, heteroaryl, —O-aryl, or —O-heteroaryl;

in the presence of a catalyst to form a compound of formula III:

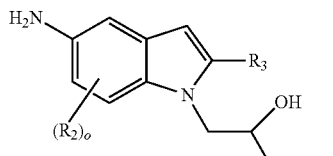

III wherein, independently for each occurrence:
- $R_2$ is —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
- $R^J$ is hydrogen or $C_{1-6}$ aliphatic;
- $R_3$ is $C_{1-6}$ aliphatic optionally substituted with OH, OP, —O—$C_{1-6}$ aliphatic, aryl, heteroaryl, —O-aryl, or —O-heteroaryl;
- P is a protecting group; and
- o is an integer from 0 to 3;

e) reacting the compound of formula III in a fourth organic solvent with a compound of formula II:

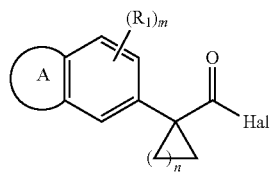

II wherein, independently for each occurrence:
- ring A is a fused cycloalkyl, heterocycloalkyl, aryl, or heteroaryl ring;
- Hal is a halide;
- $R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
- $R^J$ is hydrogen or $C_{1-6}$ aliphatic;
- m is an integer from 0 to 3 inclusive; and
- n is an integer from 1 to 4 inclusive;

to form the compound of formula IV.

In another embodiment, the invention features the above method wherein in formula IV, ring A is selected from

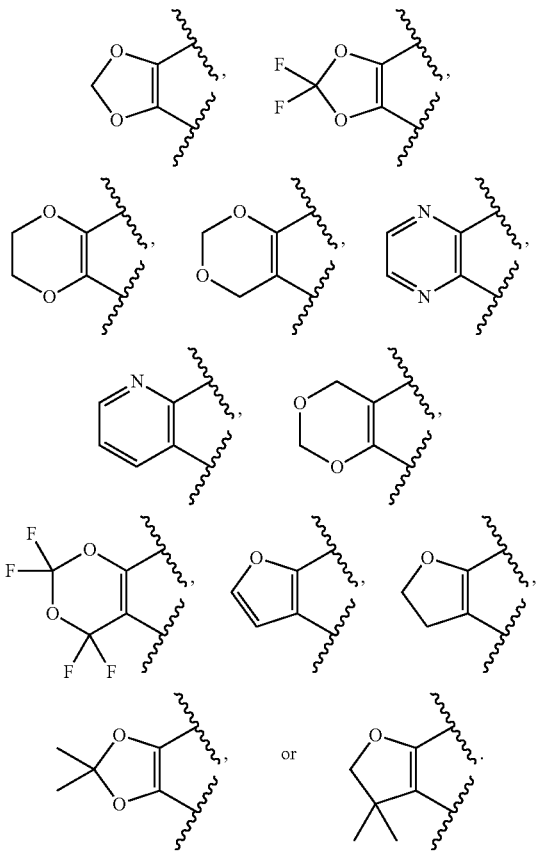

In another embodiment, in formula IV, ring A is

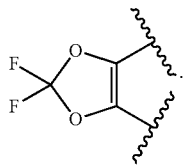 [SMILES: *C1=C(*)OC(F)(F)O1]

In another embodiment, the invention features the above method wherein in formula IV, m is 0. In another embodiment, in formula IV, n is 1. In another embodiment, in formula IV, o is 1 and $R_2$ is F.

In another embodiment, the invention features the above method wherein in formula IV, P is benzyl.

In another embodiment, the invention features the above method wherein in formula IV, $R_3$ is a $C_4$ aliphatic optionally substituted with OP. In another embodiment, in formula IV, $R_3$ is

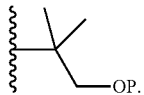

In another embodiment, in formula IV, $R_3$ is

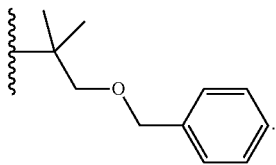

In another embodiment, the invention features the above method wherein in formula IV, ring A is

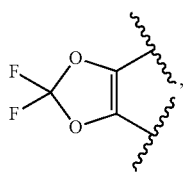

m is 0, n is 1, o is 1 and $R_2$ is F, P is benzyl, and $R_3$ is

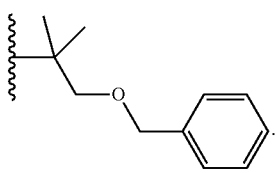 [SMILES: *C(C)(C)COCc1ccccc1]

In another embodiment, the invention features the above method wherein in step a), the halogenating reagent is N-bromosuccinimide.

In another embodiment, the invention features the above method wherein in step a), the first organic solvent is an aprotic solvent. In another embodiment, in step a), the first organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, in step a), the first organic solvent is ethyl acetate.

In another embodiment, the invention features the above method wherein step a) takes place at about 2° C. to 42° C. In another embodiment, step a) takes place at about 12° C. to 32° C. In another embodiment, step a) takes place at about 22° C.

In another embodiment, the invention features the above method wherein in formula IIIB, o is 1, $R_2$ is F, and Hal is Br.

In another embodiment, the invention features the above method wherein in formula IIIC, P is benzyl.

In another embodiment, the invention features the above method wherein in step b), the second organic solvent is an aprotic solvent. In another embodiment, in step b), the second organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, in step b), the second organic solvent is toluene.

In another embodiment, the invention features the above method wherein in step b), the reaction with a compound of formula IIIC takes place at about 60° C. to 100° C. In another embodiment, in step b), the reaction with a compound of formula IIIC takes place at about 70° C. to 90° C. In another embodiment, in step b), the reaction with a compound of formula IIIC takes place at about 80° C.

In another embodiment, the invention features the above method wherein in step b), reduction is carried out with hydrogen.

In another embodiment, the invention features the above method wherein in step b), the acid is p-toluenesulfonic acid.

In another embodiment, the invention features the above method wherein in formula IIID, o is 1, $R_2$ is F, Hal is Br, $A^-$ is Tos$^-$, and P is benzyl.

In another embodiment, the invention features the above method wherein in formula IIIE, $R_3$ is $C(CH_3)_2CH_2O$(benzyl).

In another embodiment, the invention features the above method wherein in step c), the base is an inorganic base.

In another embodiment, the invention features the above method wherein in step c), the base is $NaHCO_3$.

In another embodiment, the invention features the above method wherein in step d), the third organic solvent is an aprotic solvent. In another embodiment, in step d), the third organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, in step d), the third organic solvent is acetonitrile.

In another embodiment, the invention features the above method wherein step d) takes place at about 60° C. to 100° C. In another embodiment, step d) takes place at about 70° C. to 90° C. In another embodiment, step d) takes place at about 80° C.

In another embodiment, the invention features the above method wherein in step d), the catalyst is a palladium catalyst. In another embodiment, in step d), the catalyst is selected from palladium(II)acetate, Pd(dppf)Cl$_2$, Pd(dba)$_2$, tetrakis(triphenylphosphine)palladium(0) or tris(dibenzylideneacetone)dipalladium(0). In another embodiment, in step d), the catalyst is palladium(II)acetate.

In another embodiment, the invention features the above method wherein in step e), ring A is

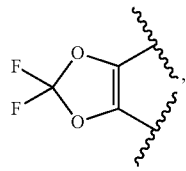

m is 0, n is 1, and Hal is Cl.

In another embodiment, the invention features the above method wherein in step e), the fourth organic solvent is an aprotic solvent. In another embodiment, in step e), the fourth organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, ethyl acetate, dichloromethane, or dimethylsulfoxide. In another embodiment, in step e), the fourth organic solvent is dichloromethane.

In another embodiment, the invention features the above method wherein step e) takes place at about −20° C. to 20° C. In another embodiment, step e) takes place at about −10° C. to 10° C. In another embodiment, step e) takes place at about 0° C.

In another embodiment, the invention features the above method wherein in step e), the compound of formula II is prepared in situ by halogenating the acid precursor and reacted with the compound of formula III without isolation.

In another embodiment, the invention features the above method further comprising removing the two protecting groups from the compound of formula IV to form a compound of formula IVA:

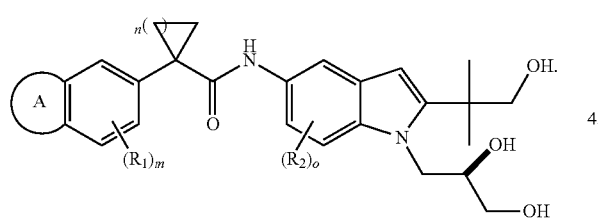

IVA

In another embodiment, the protecting groups are removed by hydrogenation.

In another aspect, the invention features a method of preparing Compound 1:

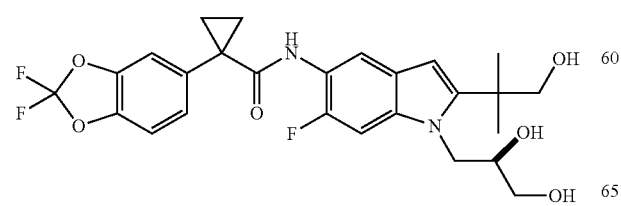

1 comprising the steps of:

a) reacting compound 2:

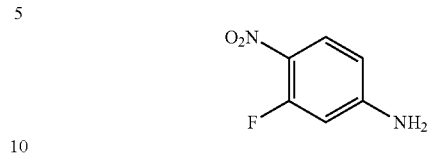

2 with a brominating reagent to form a compound 3:

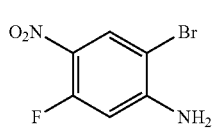

3 b) reacting compound 3 with compound 4:

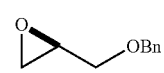

4 followed by reduction to form compound 5:

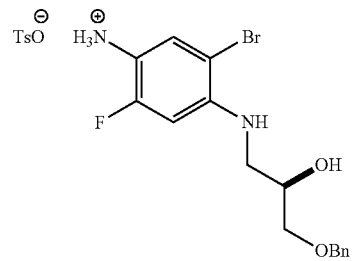

5 followed by neutralizing compound 5 with a base to give compound 5a:

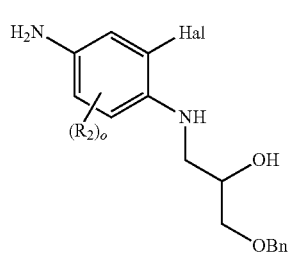

5a c) reacting compound 5a with compound 6:

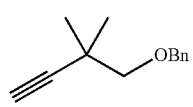

in the presence of a catalyst to form compound 7:

7

[Structure of compound 7: H2N, F, OBN, OH, OBN substituted indole]

d) reacting compound 7 with compound 8:

8

[Structure of compound 8: difluorobenzodioxole-cyclopropane-carbonyl chloride]

to form compound 9:

9

[Structure of compound 9]

and e) removing the two Bn protecting groups to form Compound 1.

In another embodiment, the invention features the above method wherein in step a), the brominating agent is N-bromosuccinimide.

In another embodiment, the invention features the above method wherein in setp b), the reduction is carried out with hydrogen.

In another embodiment, the invention features the above method wherein in setp b), the base is an inorganic base.

In another embodiment, the invention features the above method wherein in setp b), the base is $NaHCO_3$.

In another embodiment, the invention features the above method wherein in step c), the catalyst is a palladium catalyst. In another embodiment, in step c), the catalyst is selected from palladium(II)acetate, $Pd(dppf)Cl_2$, $Pd(dba)_2$, tetrakis(triphenylphosphine)palladium(0) or tris(dibenzylideneacetone)dipalladium(0). In another embodiment, in step c), the catalyst is palladium(II)acetate.

In another embodiment, the invention features the above method wherein in step d), compound 8 is made in situ by halogenating the acid precursor without isolation.

In another embodiment, the invention features the above method wherein in step e), the Bn protecting groups are removed by hydrogenation.

In another aspect, the invention features a compound of formula 23:

23

[Structure of formula 23 with ring A, $(R_1)_m$, X, $OR^J$]

wherein:

ring A is a fused cycloalkyl, heterocycloalkyl, aryl, or heteroaryl ring;

$R_1$ is independently selected from $-R^J$, $-OR^J$, $-N(R^J)_2$, $-NO_2$, halogen, $-CN$, $-C_{1-4}$haloalkyl, $-C_{1-4}$haloalkoxy, $-C(O)N(R^J)_2$, $-NR^JC(O)R^J$, $-SOR^J$, $-SO_2R^J$, $-SO_2N(R^J)_2$, $-NR^JSO_2R^J$, $-COR^J$, $-CO_2R^J$, $-NR^JSO_2N(R^J)_2$, $-COCOR^J$;

$R^J$ is hydrogen or $C_{1-6}$ aliphatic;

X is CN or $CO_2R$;

R is $C_{1-6}$ aliphatic or aryl; and m is an integer from 0 to 3 inclusive.

In another embodiment, the invention features a compound of formula 23 and the attendant definitions, wherein ring A is a fused heterocycloalkyl or heteroaryl. In another embodiment, ring A is selected from

[Various fused ring structures: methylenedioxy, difluoromethylenedioxy, dioxane, dioxine, pyrazine, pyridine, dioxine variants, difluorodioxane, furan, dihydrofuran, dimethyldioxole, dimethyldihydrofuran]

or

In another embodiment, ring A is

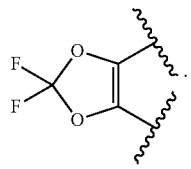

In another embodiment, the invention features a compound of formula 23 and the attendant definitions, wherein X is CN. In another embodiment, X is CO₂Et.

In another embodiment, the invention features a compound of formula 23 and the attendant definitions, wherein m is 0.

In another embodiment, the invention features a compound of formula 23 and the attendant definitions, wherein $R^J$ is $C_{1-6}$ aliphatic. In another embodiment, $R^J$ is —CH₂CH₃.

In another aspect, the invention features the compound

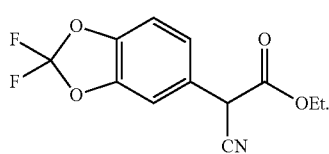 [SMILES: CCOC(=O)C(C#N)c1ccc2c(c1)OC(F)(F)O2]

In another aspect, the invention features the compound

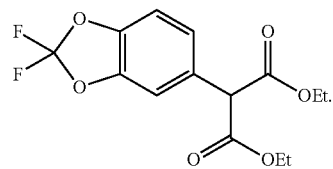 [SMILES: CCOC(=O)C(C(=O)OCC)c1ccc2c(c1)OC(F)(F)O2]

Methods of Preparing Compounds of Formulas I, II, III, and IV

Compounds of formulas I, II, II, and IV may be prepared by the methods of Schemes 1-3.

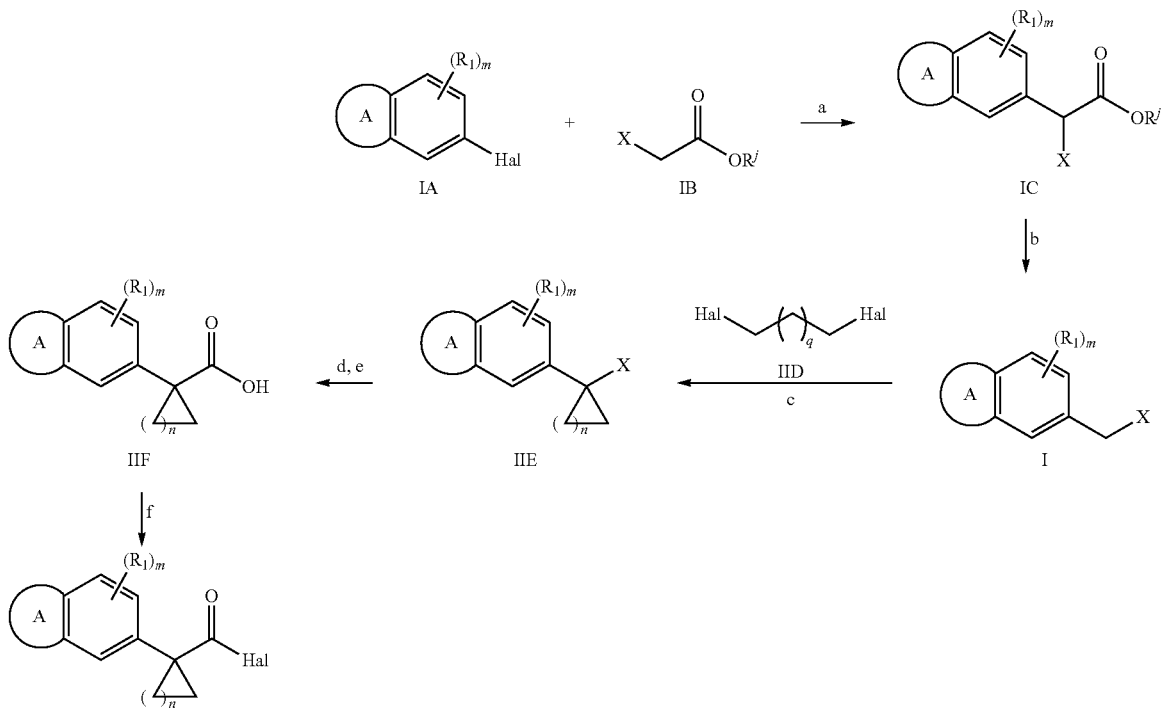

Scheme 1. Compounds of formula I and II.

a = Pd(0) catalyst; b = acid; c = base; d = hydroxide base; e = acid; f = halogenating agent;

wherein ring A, $R_1$, m, X, $R^J$, Hal, q, and n are as defined above.

In Scheme 1, aryl halide IA is reacted with ester IB in the presence of a transition metal catalyst in a suitable solvent (e.g. toluene) to produce ester IC. In esters IB and IC, X can either be CN or CO₂R. Treatment of IC with an acid in a suitable solvent (e.g. dimethyl sulfoxide (DMSO)) produces I. Reaction of I with the dihalide IID in the presence of base gives the cycloalkylidene IIE. Hydrolization of the cyanide or remaining ester group depending on the identity of X gives the carboxylic acid IIF which is halogenated to yield the acid halide II.

In one embodiment, IA is commercially available. In one embodiment, ring A is a 5 membered dioxyl ring. In one embodiment, Hal in IA is Br. In one embodiment, the reaction of IA and IIB takes place in toluene in the presence of a Pd(0) caystalyst, e.g. Pd(dba)₂. In a further embodiment, the reaction takes place in the presence of an alkyl phosphine, e.g. t-Bu$_3$P and phosphate salt, e.g. Na$_3$PO$_4$. In another embodiment, the reaction of IA and IIB takes place at about 70° C. In another embodiment, R$^J$ is Et.

In one embodiment, the de-esterification of IC to I is done with an inorganic acid. In a further embodiment, the inorganic acid is HCl. The conversion takes place in an appropriate aprotic solvent (e.g. DMSO) at about 75° C.

In one embodiment, I is reacted with NaOH and an alkyl dihalide to yield the cycloalkylidene in a suitable solvent (e.g. MTBE). The process is adaptable to several spirocyclic rings by choosing the appropriate alkyl dihalide. For example, a spirocylic butane ring can be produced by reacting I with, for example, 1-bromo-3-chloropropane. It has been found that a mixed bromo and chloro dihalide works best on an economic scale as it is believed that the thermodynamics of the reaction are more favorable.

In one embodiment, IIE is hydrolized to the carboxylic acid IIF in the presence of water and a base (e.g. NaOH) in a suitable solvent (e.g. ethanol). Subseqent treatment with an acid such as HCl yields IIF. In another embodiment, IIF is worked up by recrystallizing it from toluene.

In one embodiment, the halogenating agent that converts IIF to II is thionyl chloride. In another embodiment, the thionyl chloride is added to IIF in toluene at about 60° C. In one embodiment, this step directly proceeds the coupling between II and amine III (see below) and is carried out in the same reaction vessel.

There are several non-limiting advantages to forming II according to Scheme 1 and the embodiments described above and elsewhere in the application. These advantages are apparent even more so when manufacturing II on an economic scale and include the following. The overall reaction requires only 5 steps, which is less than what's been previously reported (i.e. starting from an aryl carboxylic acid, which is reduced to the methyl alcohol, which is converted to a methyl chloride, which is reacted with NaCN). This synthetic route introduces the CN or ester group (i.e. X) without a separate chlorinating reaction. Using ethanol as the cosolvent in hydrolyzing IIE to IIF results in a homogeneous reaction mixture making sampling and monitoring the reaction easier. Recrystallizing IIF from toluene eliminates the need for forming a dicyclohexy-lamine (DCA) salt as previously reported.

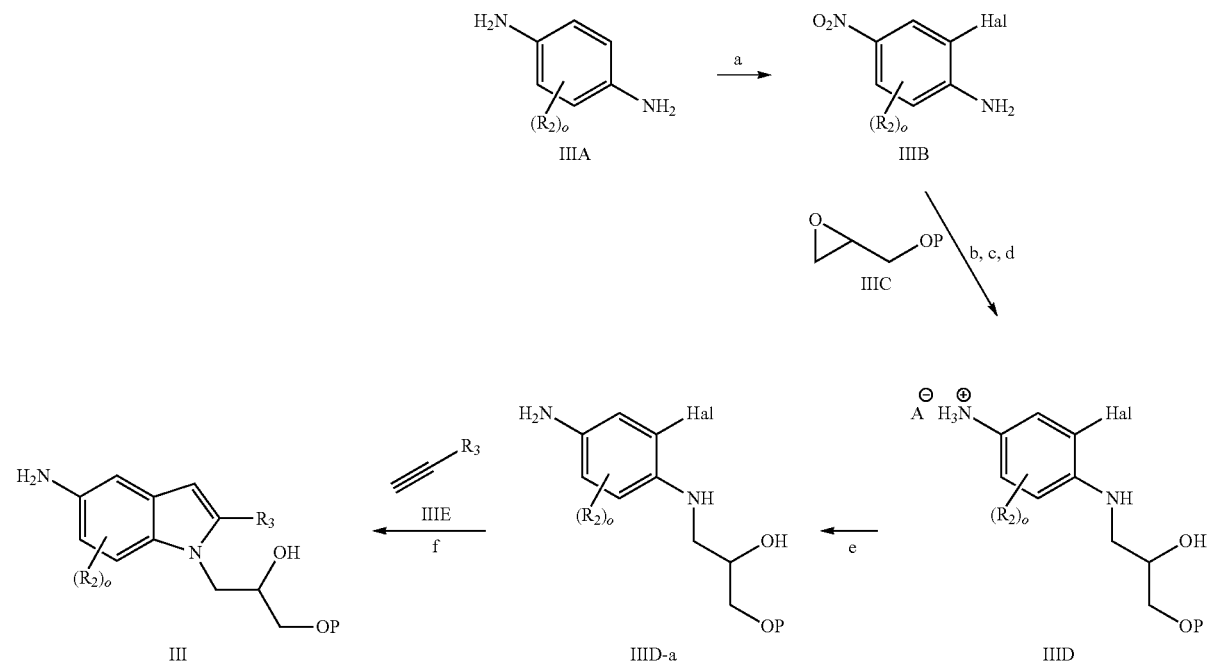

Scheme 2. Compounds of formula III.

a = halogenating agent; b = Zn(II) catalyst; c = H$_2$, Pt; d = acid; e = base; f = Pd(II) catalyst;

wherein R$_2$, o, Hal, A$^\ominus$, and P are defined as above.

In one embodiment, in IIIA, R$_2$ is F and is meta to the amine group. In another embodiment, IIIA is brominated with N-bromosuccinimide in a suitable solvent (e.g. ethylacetate) at about 22° C.

In another embodiment, IIIB is reacted with epoxide IIIC effecting a ring opening reaction with the amine group of IIIB to form IIID. In one embodiment, the protecting group, P, in IIIC is benzyl (Bn). In another embodiment epoxide IIIC is chiral. In one embodiment IIIC is (R) IIIC. In another embodiment, IIIC is (S) IIIC. In one embodiment, the ring opening reaction is carried out in a suitable solvent (e.g. toluene) at about 80° C. In another embodiment, the ring opening reaction takes place in the presence of a Zn(II) catalyst (e.g. Zn(ClO$_4$)$_2$). In another embodiment, the conversion from IIIB to IIID comprises the ring opening reaction with epoxide IIIC, followed by hydrogenation, and then treatment with an acid to form IIID. In a further embodiment, hydrogenation is carried out with H$_2$/Pt(S)/C. In a further embodiment, the acid is toluene sulfonic acid, such that A$^\ominus$ is a tosylate anion.

In another embodiment, alkyne IIIE is coupled with IIID in a suitable solvent (e.g. acetonitrile) at about 80° C. In another embodiment, the coupling reaction takes place in the presence of a Pd(II) catalyst, such as Pd(OAc)$_2$. The initial reaction does not result in ring closure, only replacement of the halide on IIID. Ring closure is accomplished through reaction with another Pd(II) catalyst, such as (MeCN)$_2$PdCl$_2$ in a suitable solvent (e.g. acetonitrile). In one embodiment, ring closure takes place at about 80° C. In one embodiment, R$_3$ in alkyne IIIE is —C(CH$_3$)$_2$CH$_2$OBn. In one embodiment, the product from the coupling reaction is not isolated but taken up in acetonitrile and reacted with (MeCN)$_2$PdCl$_2$.

There are several non-limiting advantages to forming compound III according to Scheme 2 and the embodiments described above and elsewhere in the application. These advantages are apparent even more so when manufacturing III on an economic scale and include the following. The overall number of steps have been reduced compared to what was disclosed previously to just 3 steps. Other advantages include the elimination of chromatography and by-products from protecting groups.

Scheme 3. Compounds of Formula IV.

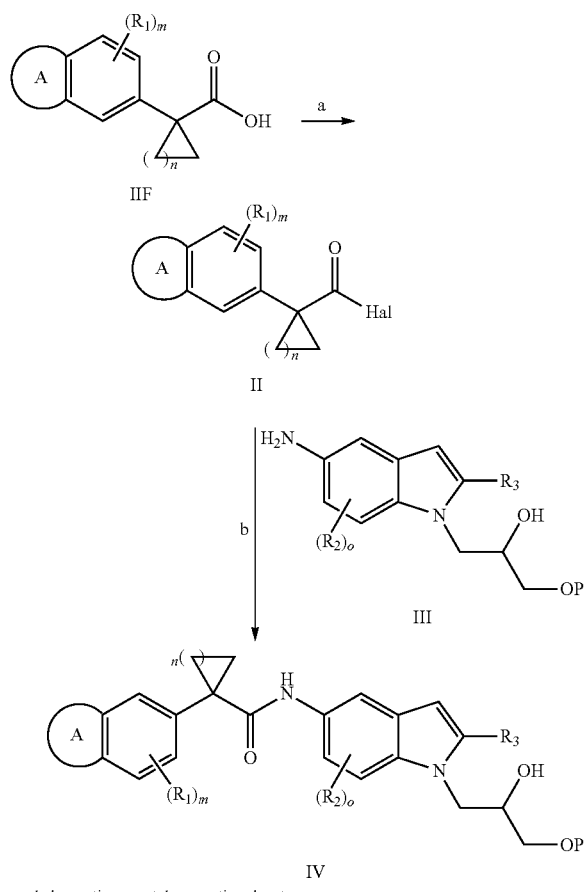

a = halogenating agent; b = aprotic solvent;

wherein ring A, R$_1$, m, n, hal, R$_2$, o, P, and R$_3$ are as defined above.

An acid-base reaction between II and III in a suitable solvent (e.g. dichloromethane (DCM)) yields the protected analog of Compound 1. In one embodiment, the acid halide II is prepared from IIF as depicted in Scheme 1 in the same reaction vessel and is not isolated. In another embodiment, the acid-based reaction is carried out in the presence of a base such as triethylamine (TEA). In one embodiment, the amount of TEA is 2 equivalents relative to II. In one embodiment, after a reaction time of about 4 hours at about 0° C. and warming to room temperature overnight, water is added to the mixture and stirred for an additional 30 minutes. The organic phase is separated and IV is isolated by distilling off the reaction solvent. In one embodiment, IV is collected by silica pad filtration.

In another embodiment, compounds of formula IV may be deprotected to form compounds of formula IVa according to Scheme 4.

Scheme 4. Deprotecting Compounds of Formula IV.

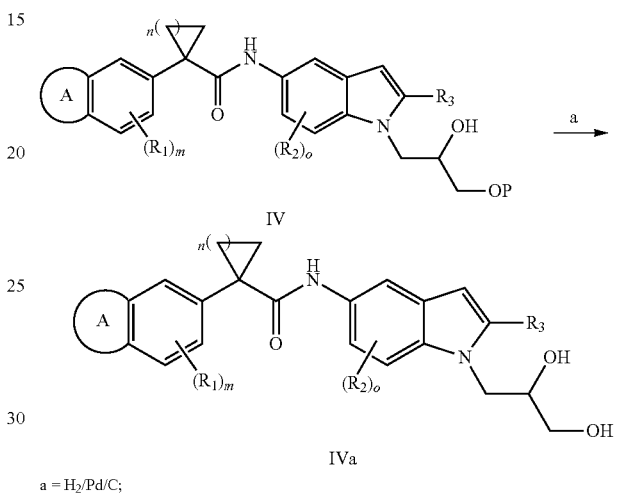

a = H$_2$/Pd/C;

wherein ring A, R$_1$, m, n, R$_2$, o, R$_3$, and P are defined as above.

In one embodiment, hydrogen pressurization is 3 Bars. In another embodiment, the hydrogenation agitation rate is increased to 800 rpm. In another embodiment, after rapid hydrogen uptake subsides, the hydrogenation vessel is heated to about 50° C. for 2 days. In another embodiment, after the 2 days, more catalyst is added and hydrogenation continues for another 4 days. In another embodiment, IV is dissolved in a suitable solvent (e.g. THF).

In another embodiment, Compound 1 may be prepared by coupling the acid halide moiety 7 with the amine moiety 8 to form compound 9 followed by deprotection according to Scheme 5.

Scheme 5. Preparation of Compound 1.

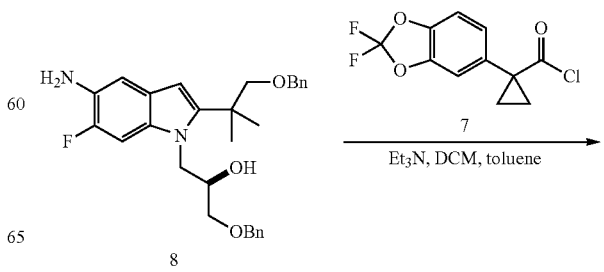

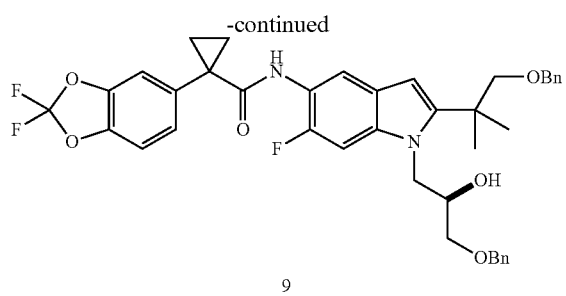
Wherein Compound 8 is prepared according to Scheme 7.
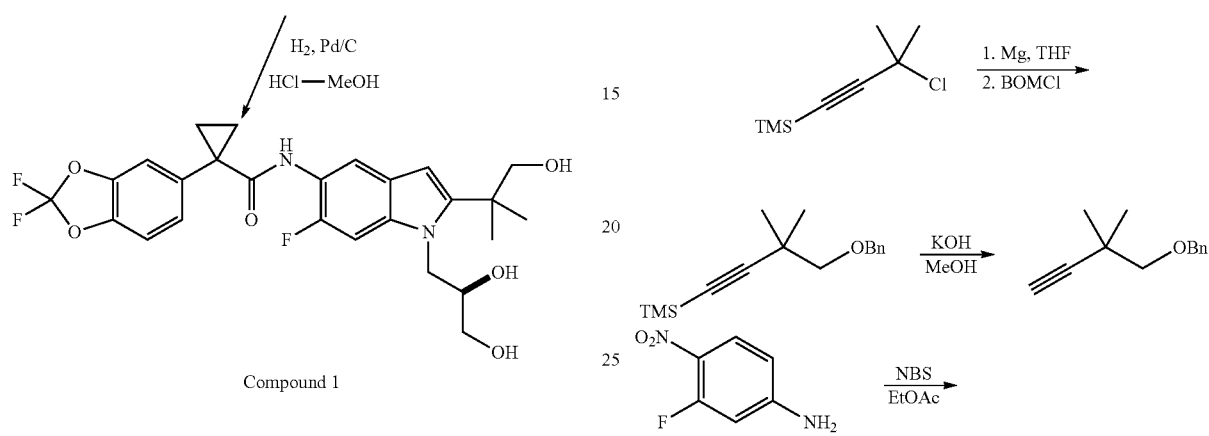
Wherein Compound 7 is prepared according to Scheme 6.
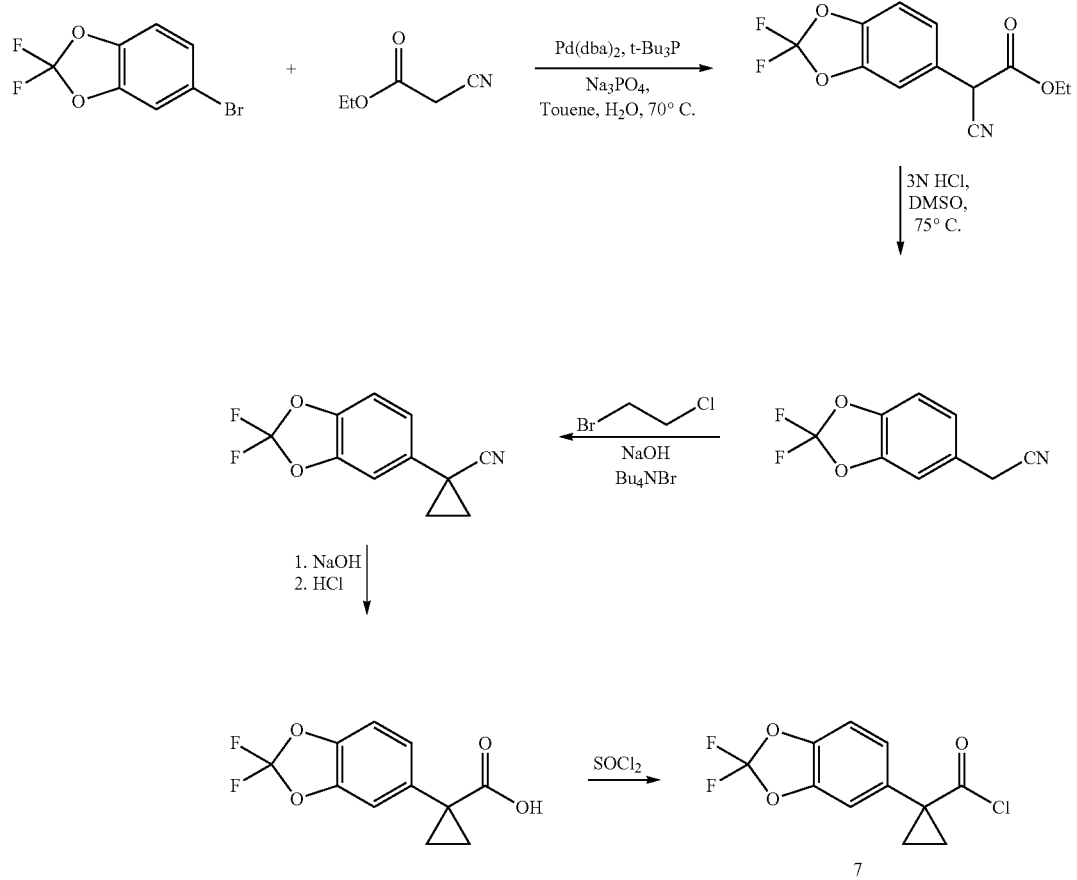

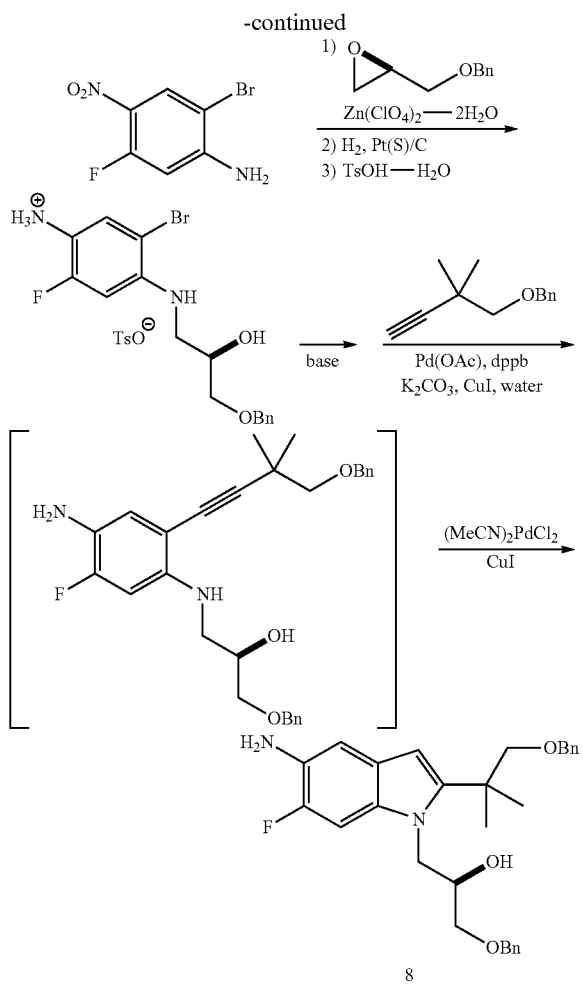

Uses, Formulation and Administration

Pharmaceutically Acceptable Compositions

In another aspect of the present invention, pharmaceutically acceptable compositions are provided, wherein these compositions comprise Compound 1 Form A or amorphous Compound 1 as described herein, and optionally comprise a pharmaceutically acceptable carrier, adjuvant or vehicle. In certain embodiments, these compositions optionally further comprise one or more additional therapeutic agents.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating a condition, disease, or disorder implicated by CFTR. In certain embodiments, the present invention provides a method of treating a condition, disease, or disorder implicated by a deficiency of CFTR activity, the method comprising administering a composition comprising a Compound 1 described herein to a subject, preferably a mammal, in need thereof.

A "CFTR-mediated disease" as used herein is a disease selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, Osteoporosis, Osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, hyperekplexia, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia. In another embodiment, the CFTR mediated disease is cystic fibrosis, emphysema, COPD, or osteoporosis. In another embodiment, the CFTR mediated disease is cystic fibrosis.

In certain embodiments, the present invention provides a method of treating a CFTR-mediated disease in a human comprising the step of administering to said human an effective amount of a composition comprising Compound 1 described herein.

According to the invention an "effective amount" of Compound 1 Form A or amorphous Compound 1 or a pharmaceutically acceptable composition thereof is that amount effective for treating or lessening the severity of any of the diseases recited above.

Compound 1 or a pharmaceutically acceptable composition thereof may be administered using any amount and any route of administration effective for treating or lessening the severity of one or more of the diseases recited above.

In certain embodiments, Compound 1 described herein or a pharmaceutically acceptable composition thereof is useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508.

In one embodiment, Compound 1 described herein or a pharmaceutically acceptable composition thereof is useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Tansmembrane Conductance Regulator Defects and Opportunities of Therapy*; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, Compound 1 described herein or a pharmaceutically acceptable composition thereof is useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic insufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient" or "subject", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

In certain embodiments, the dosage amount of Compound 1 in the dosage unit form is from 100 mg to 1,000 mg. In another embodiment, the dosage amount of Compound 1 is from 200 mg to 900 mg. In another embodiment, the dosage amount of Compound 1 is from 300 mg to 800 mg. In another embodiment, the dosage amount of Compound 1 is from 400 mg to 700 mg. In another embodiment, the dosage amount of Compound 1 is from 500 mg to 600 mg.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

It will also be appreciated that Compound 1 described herein or a pharmaceutically acceptable composition thereof can be employed in combination therapies, that is, Compound 1 can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

In one embodiment, the additional agent is selected from a mucolytic agent, bronchodialator, an anti-biotic, an anti-infective agent, an anti-inflammatory agent, a CFTR modulator other than a compound of the present invention, or a nutritional agent.

In one embodiment, the additional therapeutic agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional agent is a mucolyte. Exemplary mucolytes useful herein includes Pulmozyme®.

In another embodiment, the additional agent is a bronchodialator. Exemplary bronchodialtors include albuterol, metaprotenerol sulfate, pirbuterol acetate, salmeterol, or tetrabuline sulfate.

In another embodiment, the additional agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[(3S, 5R)-5-(4-amino-2-oxopyrimidin-1-yl)-3-hydroxyoxolan-2-yl]methoxy-hydroxyphosphoryl][[[(2R,3S,4R,5R)-5-(2,4-dioxopyrimidin-1-yl)-3,4-dihydroxyoxolan-2-yl]methoxy-hydroxyphosphoryl]oxy-hydroxyphosphoryl]hydrogen phosphate), or bronchitol (inhaled formulation of mannitol).

In another embodiment, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In another embodiment, the additional agent is a CFTR modulator other than Compound 1, i.e., an agent that has the effect of modulating CFTR activity. Exemplary such agents include ataluren ("PTC124®"; 3-[5-(2-fluorophenyl)-1,2,4-oxadiazol-3-yl]benzoic acid), sinapultide, lancovutide, depelestat (a human recombinant neutrophil elastase inhibitor), cobiprostone (7-{(2R, 4aR, 5R, 7aR)-2-[(3S)-1,1-difluoro-3-methylpentyl]-2-hydroxy-6-oxooctahydrocyclopenta[b]pyran-5-yl}heptanoic acid), and N-(5-hydroxy-2,4-ditert-butyl-phenyl)-4-oxo-1H-quinoline-3-carboxamide.

In another embodiment, the additional agent is a nutritional agent. Exemplary nutritional agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

In another embodiment, the additional agent is a compound selected from gentamicin, curcumin, cyclophosphamide, 4-phenylbutyrate, miglustat, felodipine, nimodipine, Philoxin B, geniestein, Apigenin, cAMP/cGMP modulators such as rolipram, sildenafil, milrinone, tadalafil, aminone, isoproterenol, albuterol, and almeterol, deoxyspergualin, HSP 90 inhibitors, HSP 70 inhibitors, proteosome inhibitors such as epoxomicin, lactacystin, etc.

In another embodiment, the additional agent is a compound disclosed in WO 2004028480, WO 2004110352, WO 2005094374, WO 2005120497, or WO 2006101740.

In another embodiment, the additional agent is a benzo(c) quinolizinium derivative that exhibits CFTR modulation activity or a benzopyran derivative that exhibits CFTR modulation activity.

In another embodiment, the additional agent is a compound disclosed in U.S. Pat. Nos. 7,202,262, 6,992,096, US20060148864,US20060148863,US20060035943, US20050164973, WO2006110483, WO2006044456, WO2006044682, WO2006044505, WO2006044503, WO2006044502, or WO2004091502.

In another embodiment, the additional agent is a compound disclosed in WO2004080972, WO2004111014, WO2005035514, WO2005049018, WO2006099256, WO2006127588, or WO2007044560.

These combinations are useful for treating the diseases described herein including cystic fibrosis. These combinations are also useful in the kits described herein.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In order that the invention described herein may be more fully understood, the following examples are set forth. It should be understood that these examples are for illustrative purposes only and are not to be construed as limiting this invention in any manner.

EXAMPLES

Methods & Materials

Vitride® (sodium bis(2-methoxyethoxy)aluminum hydride [or NaAlH$_2$(OCH$_2$CH$_2$OCH$_3$)$_2$], 65 wgt % solution in toluene) was purchased from Aldrich Chemicals. 3-Fluoro-4-nitroaniline was purchased from Capot Chemicals. 5-Bromo-2,2-difluoro-1,3-benzodioxole was purchased from Alfa Aesar. 2,2-Difluoro-1,3-benzodioxole-5-carboxylic acid was purchased from Saltigo (an affiliate of the Lanxess Corporation).

Anywhere in the present application where a name of a compound may not correctly describe the structure of the compound, the structure supersedes the name and governs.

Synthesis of Compound 1

Acid Moiety

Synthesis of (2,2-difluoro-1,3-benzodioxol-5-yl)-1-ethylacetate-acetonitrile

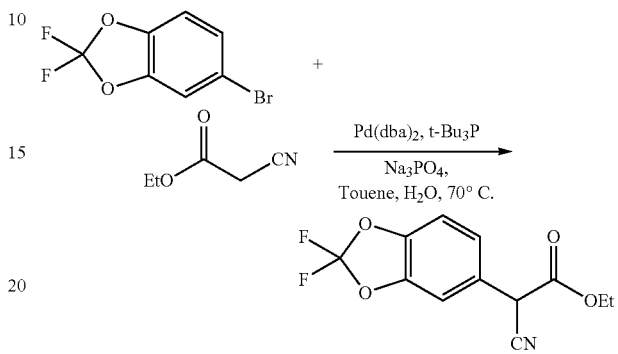

A reactor was purged with nitrogen and charged with 900 mL of toluene. The solvent was degassed via nitrogen sparge for no less than 16 h. To the reactor was then charged Na$_3$PO$_4$ (155.7 g, 949.5 mmol), followed by bis(dibenzylideneacetone) palladium (0) (7.28 g, 12.66 mmol). A 10% w/w solution of tert-butylphosphine in hexanes (51.23 g, 25.32 mmol) was charged over 10 min at 23° C. from a nitrogen purged addition funnel. The mixture was allowed to stir for 50 min, at which time 5-bromo-2,2-difluoro-1,3-benzodioxole (75 g, 316.5 mmol) was added over 1 min. After stirring for an additional 50 min, the mixture was charged with ethyl cyanoacetate (71.6 g, 633.0 mmol) over 5 min followed by water (4.5 mL) in one portion. The mixture was heated to 70° C. over 40 min and analyzed by HPLC every 1-2 h for the percent conversion of the reactant to the product. After complete conversion was observed (typically 100% conversion after 5-8 h), the mixture was cooled to 20-25° C. and filtered through a celite pad. The celite pad was rinsed with toluene (2×450 mL) and the combined organics were concentrated to 300 mL under vacuum at 60-65° C. The concentrate was charged with 225 mL DMSO and concentrated under vacuum at 70-80° C. until active distillation of the solvent ceased. The solution was cooled to 20-25° C. and diluted to 900 mL with DMSO in preparation for Step 2. $^1$H NMR (500 MHz, CDCl$_3$) δ 7.16-7.10 (m, 2H), 7.03 (d, J=8.2 Hz, 1H), 4.63 (s, 1H), 4.19 (m, 2H), 1.23 (t, J=7.1 Hz, 3H).

Synthesis of (2,2-difluoro-1,3-benzodioxol-5-yl)-acetonitrile

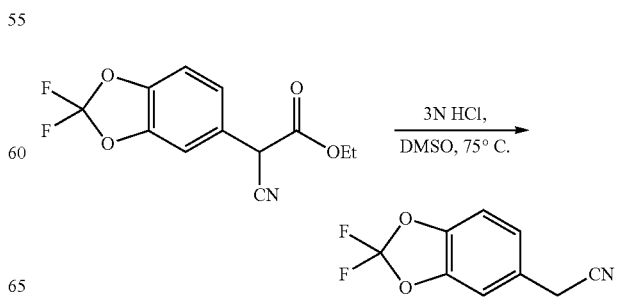

The DMSO solution of (2,2-difluoro-1,3-benzodioxol-5-yl)-1-ethylacetate-acetonitrile from above was charged with 3 N HCl (617.3 mL, 1.85 mol) over 20 min while maintaining an internal temperature <40° C. The mixture was then heated to 75° C. over 1 h and analyzed by HPLC every 1-2 h for % conversion. When a conversion of >99% was observed (typically after 5-6 h), the reaction was cooled to 20-25° C. and extracted with MTBE (2×525 mL), with sufficient time to allow for complete phase separation during the extractions. The combined organic extracts were washed with 5% NaCl (2×375 mL). The solution was then transferred to equipment appropriate for a 1.5-2.5 Torr vacuum distillation that was equipped with a cooled receiver flask. The solution was concentrated under vacuum at <60° C. to remove the solvents. (2,2-Difluoro-1,3-benzodioxol-5-yl)-acetonitrile was then distilled from the resulting oil at 125-130° C. (oven temperature) and 1.5-2.0 Torr. (2,2-Difluoro-1,3-benzodioxol-5-yl)-acetonitrile was isolated as a clear oil in 66% yield from 5-bromo-2,2-difluoro-1,3-benzodioxole (2 steps) and with an HPLC purity of 91.5% AUC (corresponds to a w/w assay of 95%). $^1$H NMR (500 MHz, DMSO) δ 7.44 (br s, 1H), 7.43 (d, J=8.4 Hz, 1H), 7.22 (dd, J=8.2, 1.8 Hz, 1H), 4.07 (s, 2H).

Synthesis of (2,2-difluoro-1,3-benzodioxol-5-yl)-cyclopropanecarbonitrile

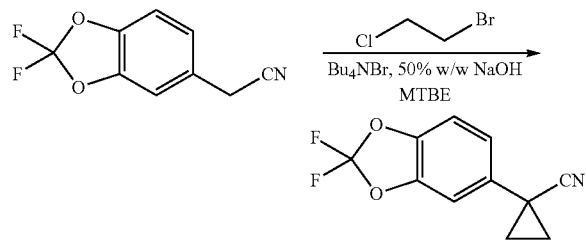

A stock solution of 50% w/w NaOH was degassed via nitrogen sparge for no less than 16 h. An appropriate amount of MTBE was similarly degassed for several hours. To a reactor purged with nitrogen was charged degassed MTBE (143 mL) followed by (2,2-difluoro-1,3-benzodioxol-5-yl)-acetonitrile (40.95 g, 207.7 mmol) and tetrabutylammonium bromide (2.25 g, 10.38 mmol). The volume of the mixture was noted and the mixture was degassed via nitrogen sparge for 30 min. Enough degassed MTBE is charged to return the mixture to the original volume prior to degassing. To the stirring mixture at 23.0° C. was charged degassed 50% w/w NaOH (143 mL) over 10 min followed by 1-bromo-2-chloroethane (44.7 g, 311.6 mmol) over 30 min. The reaction was analyzed by HPLC in 1 h intervals for % conversion. Before sampling, stirring was stopped and the phases allowed to separate. The top organic phase was sampled for analysis. When a % conversion >99% was observed (typically after 2.5-3 h), the reaction mixture was cooled to 10° C. and was charged with water (461 mL) at such a rate as to maintain a temperature <25° C. The temperature was adjusted to 20-25° C. and the phases separated. Note: sufficient time should be allowed for complete phase separation. The aqueous phase was extracted with MTBE (123 mL), and the combined organic phase was washed with 1 N HCl (163 mL) and 5% NaCl (163 mL). The solution of (2,2-difluoro-1,3-benzodioxol-5-yl)-cyclopropanecarbonitrile in MTBE was concentrated to 164 mL under vacuum at 40-50° C. The solution was charged with ethanol (256 mL) and again concentrated to 164 mL under vacuum at 50-60° C. Ethanol (256 mL) was charged and the mixture concentrated to 164 mL under vacuum at 50-60° C. The resulting mixture was cooled to 20-25° C. and diluted with ethanol to 266 mL in preparation for the next step. $^1$H NMR (500 MHz, DMSO) δ 7.43 (d, J=8.4 Hz, 1H), 7.40 (d, J=1.9 Hz, 1H), 7.30 (dd, J=8.4, 1.9 Hz, 1H), 1.75 (m, 2H), 1.53 (m, 2H).

Synthesis of 1-(2,2-difluoro-1,3-benzodioxol-5-yl)-cyclopropanecarboxylic acid

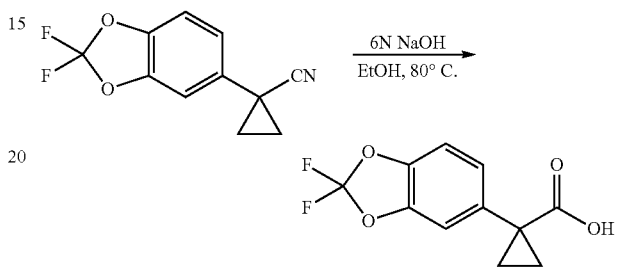

The solution of (2,2-difluoro-1,3-benzodioxol-5-yl)-cyclopropanecarbonitrile in ethanol from the previous step was charged with 6 N NaOH (277 mL) over 20 min and heated to an internal temperature of 77-78° C. over 45 min. The reaction progress was monitored by HPLC after 16 h. Note: the consumption of both (2,2-difluoro-1,3-benzodioxol-5-yl)-cyclopropanecarbonitrile and the primary amide resulting from partial hydrolysis of (2,2-difluoro-1,3-benzodioxol-5-yl)-cyclopropanecarbonitrile were monitored. When a % conversion >99% was observed (typically 100% conversion after 16 h), the reaction mixture was cooled to 25° C. and charged with ethanol (41 mL) and DCM (164 mL). The solution was cooled to 10° C. and charged with 6 N HCl (290 mL) at such a rate as to maintain a temperature <25° C. After warming to 20-25° C., the phases were allowed to separate. The bottom organic phase was collected and the top aqueous phase was back extracted with DCM (164 mL). Note: the aqueous phase was somewhat cloudy before and after the extraction due to a high concentration of inorganic salts. The organics were combined and concentrated under vacuum to 164 mL. Toluene (328 mL) was charged and the mixture condensed to 164 mL at 70-75° C. The mixture was cooled to 45° C., charged with MTBE (364 mL) and stirred at 60° C. for 20 min. The solution was cooled to 25° C. and polish filtered to remove residual inorganic salts. MTBE (123 mL) was used to rinse the reactor and the collected solids. The combined organics were transferred to a clean reactor in preparation for the next step.

Isolation of 1-(2,2-difluoro-1,3-benzodioxol-5-yl)-cyclopropanecarboxylic acid

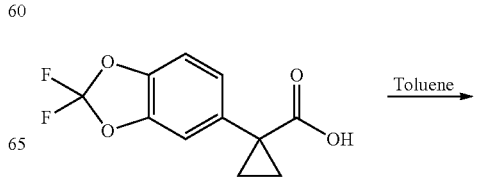

-continued

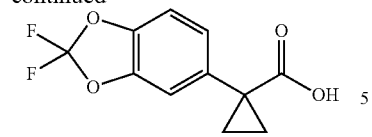

The solution of 1-(2,2-difluoro-1,3-benzodioxol-5-yl)-cyclopropanecarboxylic acid from the previous step is concentrated under vacuum to 164 mL, charged with toluene (328 mL) and concentrated to 164 mL at 70-75° C. The mixture was then heated to 100-105° C. to give a homogeneous solution. After stirring at that temperature for 30 min, the solution was cooled to 5° C. over 2 hours and maintained at 5° C. for 3 hours. The mixture was then filtered and the reactor and collected solid washed with cold 1:1 toluene/n-heptane (2×123 mL). The material was dried under vacuum at 55° C. for 17 hours to provide 1-(2,2-difluoro-1,3-benzodioxol-5-yl)-cyclopropanecarboxylic acid as an off-white crystalline solid. 1-(2,2-difluoro-1,3-benzodioxol-5-yl)-cyclopropanecarboxylic acid was isolated in 79% yield from (2,2-difluoro-1,3-benzodioxol-5-yl)-acetonitrile (3 steps including isolation) and with an HPLC purity of 99.0% AUC. ESI-MS m/z calc. 242.04, found 241.58 (M+1)$^+$; $^1$H NMR (500 MHz, DMSO) δ 12.40 (s, 1H), 7.40 (d, J=1.6 Hz, 1H), 7.30 (d, J=8.3 Hz, 1H), 7.17 (dd, J=8.3, 1.7 Hz, 1H), 1.46 (m, 2H), 1.17 (m, 2H).

Alternative Synthesis of the Acid Moiety

Synthesis of (2,2-difluoro-1,3-benzodioxol-5-yl)-methanol

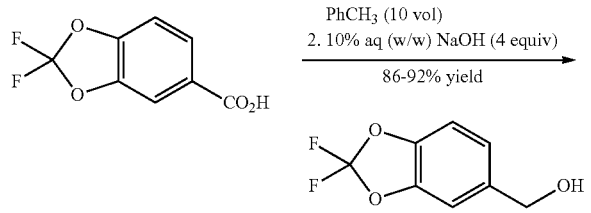

Commercially available 2,2-difluoro-1,3-benzodioxole-5-carboxylic acid (1.0 eq) is slurried in toluene (10 vol). Vitride® (2 eq) is added via addition funnel at a rate to maintain the temperature at 15-25° C. At the end of addition the temperature is increased to 40° C. for 2 h then 10% (w/w) aq. NaOH (4.0 eq) is carefully added via addition funnel maintaining the temperature at 40-50° C. After stirring for an additional 30 minutes, the layers are allowed to separate at 40° C. The organic phase is cooled to 20° C. then washed with water (2×1.5 vol), dried (Na$_2$SO$_4$), filtered, and concentrated to afford crude (2,2-difluoro-1,3-benzodioxol-5-yl)-methanol that is used directly in the next step.

Synthesis of 5-chloromethyl-2,2-difluoro-1,3-benzodioxole

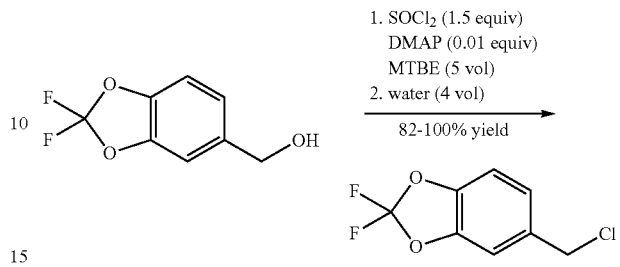

(2,2-difluoro-1,3-benzodioxol-5-yl)-methanol (1.0 eq) is dissolved in MTBE (5 vol). A catalytic amount of DMAP (1 mol %) is added and SOCl$_2$ (1.2 eq) is added via addition funnel. The SOCl$_2$ is added at a rate to maintain the temperature in the reactor at 15-25° C. The temperature is increased to 30° C. for 1 hour then cooled to 20° C. then water (4 vol) is added via addition funnel maintaining the temperature at less than 30° C. After stirring for an additional 30 minutes, the layers are allowed to separate. The organic layer is stirred and 10% (w/v) aq. NaOH (4.4 vol) is added. After stirring for 15 to 20 minutes, the layers are allowed to separate. The organic phase is then dried (Na$_2$SO$_4$), filtered, and concentrated to afford crude 5-chloromethyl-2,2-difluoro-1,3-benzodioxole that is used directly in the next step.

Synthesis of (2,2-difluoro-1,3-benzodioxol-5-yl)-acetonitrile

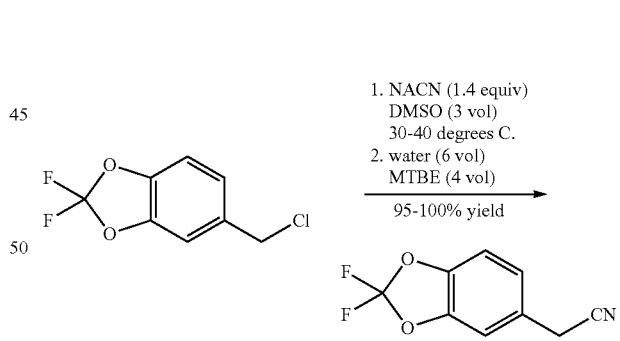

A solution of 5-chloromethyl-2,2-difluoro-1,3-benzodioxole (1 eq) in DMSO (1.25 vol) is added to a slurry of NaCN (1.4 eq) in DMSO (3 vol) maintaining the temperature between 30-40° C. The mixture is stirred for 1 hour then water (6 vol) is added followed by MTBE (4 vol). After stirring for 30 min, the layers are separated. The aqueous layer is extracted with MTBE (1.8 vol). The combined organic layers are washed with water (1.8 vol), dried (Na$_2$SO$_4$), filtered, and concentrated to afford crude (2,2-difluoro-1,3-benzodioxol-5-yl)-acetonitrile (95%) that is used directly in the next step.

The remaining steps are the same as described above for the synthesis of the acid moiety.

Amine Moiety

Synthesis of 2-bromo-5-fluoro-4-nitroaniline

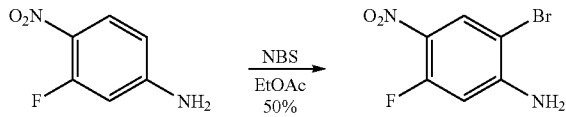 [SMILES: Nc1ccc([N+](=O)[O-])c(F)c1 ; "NBS" ; Nc1cc(F)c([N+](=O)[O-])cc1Br]

A flask was charged with 3-fluoro-4-nitroaniline (1.0 equiv) followed by ethyl acetate (10 vol) and stirred to dissolve all solids. N-Bromosuccinimide (1.0 equiv) was added as a portion-wise as to maintain internal temperature of 22° C. At the end of the reaction, the reaction mixture was concentrated in vacuo on a rotavap. The residue was slurried in distilled water (5 vol) to dissolve and remove succinimide. (The succinimide can also be removed by water workup procedure.) The water was decanted and the solid was slurried in 2-propanol (5 vol) overnight. The resulting slurry was filtered and the wetcake was washed with 2-propanol, dried in vacuum oven at 50° C. overnight with $N_2$ bleed until constant weight was achieved. A yellowish tan solid was isolated (50% yield, 97.5% AUC). Other impurities were a bromo-regioisomer (1.4% AUC) and a di-bromo adduct (1.1% AUC). $^1$H NMR (500 MHz, DMSO) δ 8.19 (1 H, d, J=8.1 Hz), 7.06 (br. s, 2 H), 6.64 (d, 1H, J=14.3 Hz).

Synthesis of p-toluenesulfonic acid salt of (R)-1-((4-amino-2-bromo-5-fluorophenyl)amino)-3-(benzyloxy)propan-2-ol

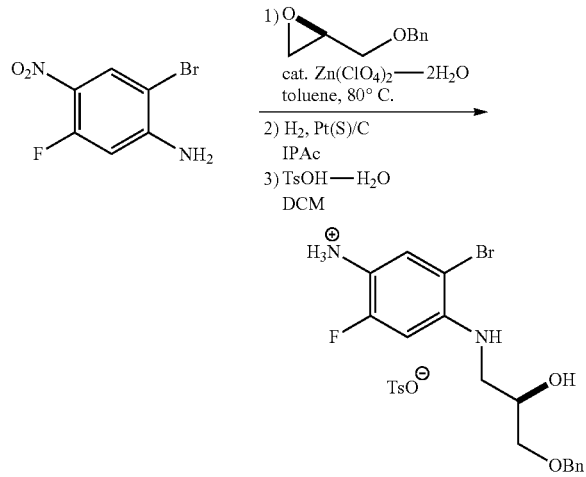

A thoroughly dried flask under $N_2$ was charged with the following: Activated powdered 4A molecular sieves (50 wt % based on 2-bromo-5-fluoro-4-nitroaniline), 2-Bromo-5-fluoro-4-nitroaniline (1.0 equiv), zinc perchlorate dihydrate (20 mol %), and toluene (8 vol). The mixture was stirred at room temperature for NMT 30 min. Lastly, (R)-benzyl glycidyl ether (2.0 equiv) in toluene (2 vol) was added in a steady stream. The reaction was heated to 80° C. (internal temperature) and stirred for approximately 7 hours or until 2-Bromo-5-fluoro-4-nitroaniline was <5% AUC.

The reaction was cooled to room temperature and Celite (50 wt %) was added, followed by ethyl acetate (10 vol). The resulting mixture was filtered to remove Celite and sieves and washed with ethyl acetate (2 vol). The filtrate was washed with ammonium chloride solution (4 vol, 20% w/v). The organic layer was washed with sodium bicarbonate solution (4 vol×2.5% w/v). The organic layer was concentrated in vacuo on a rotovap. The resulting slurry was dissolved in isopropyl acetate (10 vol) and this solution was transferred to a Buchi hydrogenator.

The hydrogenator was charged with 5 wt % Pt(S)/C (1.5 mol %) and the mixture was stirred under $N_2$ at 30° C. (internal temperature). The reaction was flushed with $N_2$ followed by hydrogen. The hydrogenator pressure was adjusted to 1 Bar of hydrogen and the mixture was stirred rapidly (>1200 rpm). At the end of the reaction, the catalyst was filtered through a pad of Celite and washed with dichloromethane (10 vol). The filtrate was concentrated in vacuo. Any remaining isopropyl acetate was chased with dichloromethane (2 vol) and concentrated on a rotavap to dryness.

The resulting residue was dissolved in dichloromethane (10 vol). p-Toluenesulfonic acid monohydrate (1.2 equiv) was added and stirred overnight. The product was filtered and washed with dichloromethane (2 vol) and suction dried. The wetcake was transferred to drying trays and into a vacuum oven and dried at 45° C. with $N_2$ bleed until constant weight was achieved. p-Toluenesulfonic acid salt of (R)-1-((4-amino-2-bromo-5-fluorophenyl)amino)-3-(benzyloxy)propan-2-ol was isolated as an off-white solid.

Chiral purity was determined to be >97% ee.

Synthesis of (3-Chloro-3-methylbut-1-ynyl)trimethylsilane

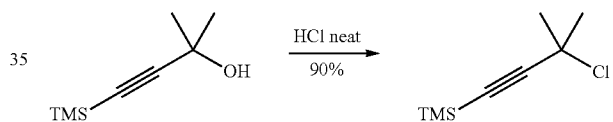

Propargyl alcohol (1.0 equiv) was charged to a vessel. Aqueous hydrochloric acid (37%, 3.75 vol) was added and stirring begun. During dissolution of the solid alcohol, a modest endotherm (5-6° C.) is observed. The resulting mixture was stirred overnight (16 h), slowly becoming dark red. A 30 L jacketed vessel is charged with water (5 vol) which is then cooled to 10° C. The reaction mixture is transferred slowly into the water by vacuum, maintaining the internal temperature of the mixture below 25° C. Hexanes (3 vol) is added and the resulting mixture is stirred for 0.5 h. The phases were settled and the aqueous phase (pH<1) was drained off and discarded. The organic phase was concentrated in vacuo using a rotary evaporator, furnishing the product as red oil.

Synthesis of (4-(Benzyloxy)-3,3-dimethylbut-1-ynyl)trimethylsilane

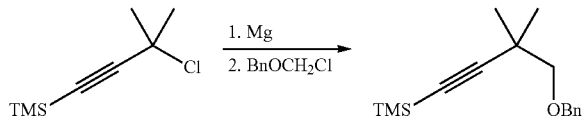

Method A

All equivalent and volume descriptors in this part are based on a 250 g reaction. Magnesium turnings (69.5 g, 2.86 mol, 2.0 equiv) were charged to a 3 L 4-neck reactor and stirred with a magnetic stirrer under nitrogen for 0.5 h. The reactor was immersed in an ice-water bath. A solution of the propargyl chloride (250 g, 1.43 mol, 1.0 equiv) in THF (1.8 L, 7.2 vol) was added slowly to the reactor, with stirring, until an initial exotherm (~10° C.) was observed. The Grignard reagent formation was confirmed by IPC using $^1$H-NMR spectroscopy. Once the exotherm subsided, the remainder of the solution was added slowly, maintaining the batch temperature <15° C. The addition required ~3.5 h. The resulting dark green mixture was decanted into a 2 L capped bottle.

All equivalent and volume descriptors in this part are based on a 500 g reaction. A 22 L reactor was charged with a solution of benzyl chloromethyl ether (95%, 375 g, 2.31 mol, 0.8 equiv) in THF (1.5 L, 3 vol). The reactor was cooled in an ice-water bath. Two Grignard reagent batches prepared as described above were combined and then added slowly to the benzyl chloromethyl ether solution via an addition funnel, maintaining the batch temperature below 25° C. The addition required 1.5 h. The reaction mixture was stirred overnight (16 h).

All equivalent and volume descriptors in this part are based on a 1 kg reaction. A solution of 15% ammonium chloride was prepared in a 30 L jacketed reactor (1.5 kg in 8.5 kg of water, 10 vol). The solution was cooled to 5° C. Two Grignard reaction mixtures prepared as described above were combined and then transferred into the ammonium chloride solution via a header vessel. An exotherm was observed in this quench, which was carried out at a rate such as to keep the internal temperature below 25° C. Once the transfer was complete, the vessel jacket temperature was set to 25° C. Hexanes (8 L, 8 vol) was added and the mixture was stirred for 0.5 h. After settling the phases, the aqueous phase (pH 9) was drained off and discarded. The remaining organic phase was washed with water (2 L, 2 vol). The organic phase was concentrated in vacuo using a 22 L rotary evaporator, providing the crude product as an orange oil.

Method B

Magnesium turnings (106 g, 4.35 mol, 1.0 eq) were charged to a 22 L reactor and then suspended in THF (760 mL, 1 vol). The vessel was cooled in an ice-water bath such that the batch temperature reached 2° C. A solution of the propargyl chloride (760 g, 4.35 mol, 1.0 equiv) in THF (4.5 L, 6 vol) was added slowly to the reactor. After 100 mL was added, the addition was stopped and the mixture stirred until a 13° C. exotherm was observed, indicating the Grignard reagent initiation. Once the exotherm subsided, another 500 mL of the propargyl chloride solution was added slowly, maintaining the batch temperature <20° C. The Grignard reagent formation was confirmed by IPC using $^1$H-NMR spectroscopy. The remainder of the propargyl chloride solution was added slowly, maintaining the batch temperature <20° C. The addition required ~1.5 h. The resulting dark green solution was stirred for 0.5 h. The Grignard reagent formation was confirmed by IPC using $^1$H-NMR spectroscopy. Neat benzyl chloromethyl ether was charged to the reactor addition funnel and then added dropwise into the reactor, maintaining the batch temperature below 25° C. The addition required 1.0 h. The reaction mixture was stirred overnight. The aqueous work-up and concentration was carried out using the same procedure and relative amounts of materials as in Method A to give the product as an orange oil.

Synthesis of 4-Benzyloxy-3,3-dimethylbut-1-yne

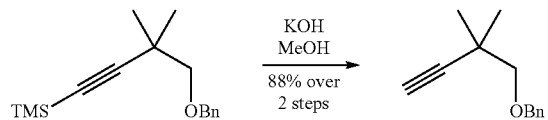 [SMILES: CC(C)(C#C[Si](C)(C)C)COCc1ccccc1 ; C#CC(C)(C)COCc1ccccc1]

A 30 L jacketed reactor was charged with methanol (6 vol) which was then cooled to 5° C. Potassium hydroxide (85%, 1.3 equiv) was added to the reactor. A 15-20° C. exotherm was observed as the potassium hydroxide dissolved. The jacket temperature was set to 25° C. A solution of 4-benzyloxy-3,3-dimethyl-1-trimethylsilylbut-1-yne (1.0 equiv) in methanol (2 vol) was added and the resulting mixture was stirred until reaction completion, as monitored by HPLC. Typical reaction time at 25° C. is 3-4 h. The reaction mixture is diluted with water (8 vol) and then stirred for 0.5 h. Hexanes (6 vol) was added and the resulting mixture was stirred for 0.5 h. The phases were allowed to settle and then the aqueous phase (pH 10-11) was drained off and discarded. The organic phase was washed with a solution of KOH (85%, 0.4 equiv) in water (8 vol) followed by water (8 vol). The organic phase was then concentrated down using a rotary evaporator, yielding the title material as a yellow-orange oil. Typical purity of this material is in the 80% range with primarily a single impurity present. $^1$H NMR (400 MHz, $C_6D_6$) δ 7.28 (d, 2 H, J=7.4 Hz), 7.18 (t, 2 H, J=7.2 Hz), 7.10 (d, 1H, J=7.2 Hz), 4.35 (s, 2 H), 3.24 (s, 2 H), 1.91 (s, 1 H), 1.25 (s, 6 H).

Synthesis of N-benzylglycolated-5-amino-2-(2-benzyloxy-1,1-dimethylethyl)-6-fluoroindole Method A Synthesis of (R)-1-((4-amino-2-(4-(benzyloxy)-3,3-dimethylbut-1-yn-1-yl)-5-fluorophenyl)amino)-3-(benzyloxy)propan-2-ol

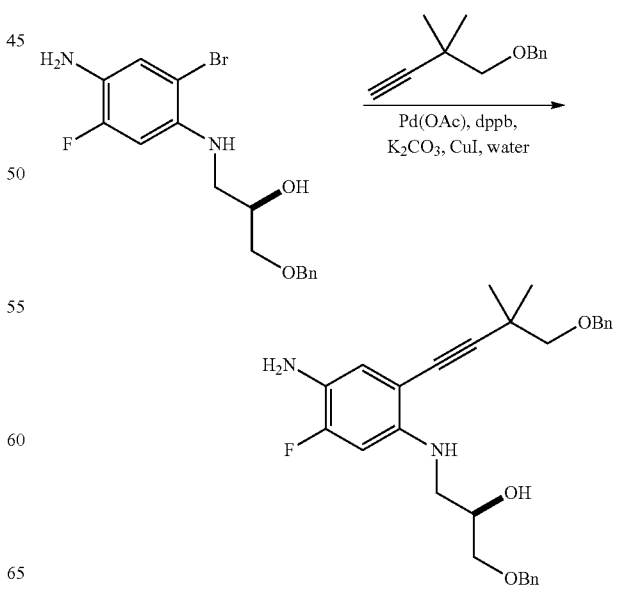

p-Toluenesulfonic acid salt of (R)-1-((4-amino-2-bromo-5-fluorophenyl)amino)-3-(benzyloxy)propan-2-ol was free-based by stirring the solid in dichloromethane (5 vol) and saturated NaHCO₃ solution (5 vol) until clear organic layer was achieved. The resulting layers were separated and the organic layer was washed with saturated NaHCO₃ solution (5 vol) followed by brine and concentrated in vacuo to obtain (R)-1-((4-amino-2-bromo-5-fluorophenyl)amino)-3-(benzyloxy)propan-2-ol free base as an oil.

Palladium acetate (0.01 eq), dppb (0.015 eq), CuI (0.015 eq) and potassium carbonate (3 eq) are suspended in acetonitrile (1.2 vol). After stirring for 15 minutes, a solution of 4-benzyloxy-3,3-dimethylbut-1-yne (1.1 eq) in acetonitrile (0.2 vol) is added. The mixture is sparged with nitrogen gas for 1 h and then a solution of (R)-1-((4-amino-2-bromo-5-fluorophenyl)amino)-3-(benzyloxy)propan-2-ol free base (1 eq) in acetonitrile (4.1 vol) is added. The mixture is sparged with nitrogen gas for another hour and then is heated to 80° C. Reaction progress is monitored by HPLC and the reaction is usually complete within 3-5 h. The mixture is cooled to room temperature and then filtered through Celite. The cake is washed with acetonitrile (4 vol). The combined filtrates are azeotroped to dryness and then the mixture is polish filtered into the next reactor. The acetonitrile solution of (R)-1-((4-amino-2-(4-(benzyloxy)-3,3-dimethylbut-1-yn-1-yl)-5-fluorophenyl)amino)-3-(benzyloxy)propan-2-ol thus obtained is used directly in the next procedure (cyclization) without further manipulation.

Synthesis of N-benzylglycolated-5-amino-2-(2-benzyloxy-1,1-dimethylethyl)-6-fluoroindole

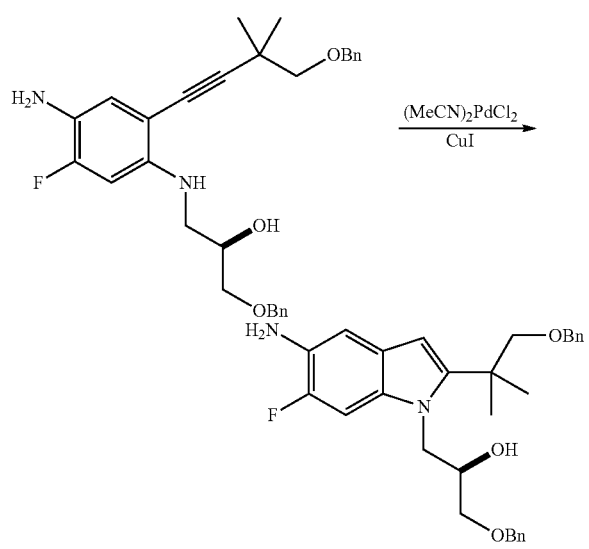

Bis-acetonitriledichloropalladium (0.1 eq) and CuI (0.1 eq) are charged to the reactor and then suspended in a solution of (R)-1-((4-amino-2-(4-(benzyloxy)-3,3-dimethylbut-1-yn-1-yl)-5-fluorophenyl)amino)-3-(benzyloxy)propan-2-ol obtained above (1 eq) in acetonitrile (9.5 vol total). The mixture is sparged with nitrogen gas for 1 h and then is heated to 80° C. The reaction progress is monitored by HPLC and the reaction is typically complete within 1-3 h. The mixture is filtered through Celite and the cake is washed with acetonitrile. A solvent swap into ethyl acetate (7.5 vol) is performed. The ethyl acetate solution is washed with aqueous NH₃—NH₄Cl solution (2×2.5 vol) followed by 10% brine (2.5 vol). The ethyl acetate solution is then stirred with silica gel (1.8 wt eq) and Si-TMT (0.1 wt eq) for 6 h. After filtration, the resulting solution is concentrated down. The residual oil is dissolved in DCM/heptane (4 vol) and then purified by column chromatography. The oil thus obtained is then crystallized from 25% EtOAc/heptane (4 vol). Crystalline (R)-1-(5-amino-2-(1-(benzyloxy)-2-methylpropan-2-yl)-6-fluoro-1H-indol-1-yl)-3-(benzyloxy)propan-2-ol is typically obtained in 27-38% yield. $^1$H NMR (400 MHz, DMSO) δ 7.38-7.34 (m, 4 H), 7.32-7.23 (m, 6 H), 7.21 (d, 1 H, J=12.8 Hz), 6.77 (d, 1H, J=9.0 Hz), 6.06 (s, 1 H), 5.13 (d, 1H, J=4.9 Hz), 4.54 (s, 2H), 4.46 (br. s, 2 H), 4.45 (s, 2 H), 4.33 (d, 1 H, J=12.4 Hz), 4.09-4.04 (m, 2 H), 3.63 (d, 1H, J=9.2 Hz), 3.56 (d, 1H, J=9.2 Hz), 3.49 (dd, 1H, J=9.8, 4.4 Hz), 3.43 (dd, 1H, J=9.8, 5.7 Hz), 1.40 (s, 6 H).

Synthesis of N-benzylglycolated-5-amino-2-(2-benzyloxy-1,1-dimethylethyl)-6-fluoroindole Method B

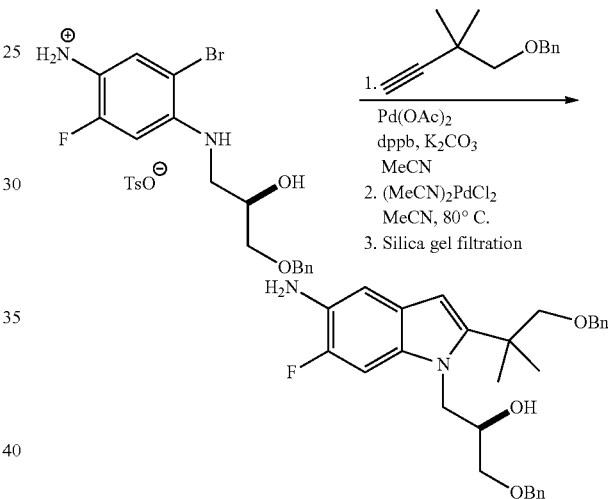

Palladium acetate (33 g, 0.04 eq), dppb (94 g, 0.06 eq), and potassium carbonate (1.5 kg, 3.0 eq) are charged to a reactor. The free based oil benzylglocolated 4-ammonium-2-bromo-5-fluoroaniline (1.5 kg, 1.0 eq) was dissolved in acetonitrile (8.2 L, 4.1 vol) and then added to the reactor. The mixture was sparged with nitrogen gas for NLT 1 h. A solution of 4-benzyloxy-3,3-dimethylbut-1-yne (70%, 1.1 kg, 1.05 eq) in acetonitrile was added to the mixture which was then sparged with nitrogen gas for NLT 1 h. The mixture was heated to 80° C. and then stirred overnight. IPC by HPLC is carried out and the reaction is determined to be complete after 16 h. The mixture was cooled to ambient temperature and then filtered through a pad of Celite (228 g). The reactor and Celite pad were washed with acetonitrile (2×2 L, 2 vol). The combined phases are concentrated on a 22 L rotary evaporator until 8 L of solvent have been collected, leaving the crude product in 7 L (3.5 vol) of acetonitrile.

Bis-acetonitriledichloropalladium (144 g, 0.15 eq) was charged to the reactor. The crude solution was transferred back into the reactor and the roto-vap bulb was washed with acetonitrile (4 L, 2 vol). The combined solutions were sparged with nitrogen gas for NLT 1 h. The reaction mixture was heated to 80° C. for NLT 16 h. In process control by HPLC shows complete consumption of starting material. The reaction mixture was filtered through Celite (300 g). The reactor and filter cake were washed with acetonitrile (3 L, 1.5 vol). The combined filtrates were concentrated to an oil by rotary evaporation. The oil was dissolved in ethyl acetate (8.8 L, 4.4 vol). The solution was washed with 20% ammonium chloride (5 L, 2.5 vol) followed by 5% brine (5 L, 2.5 vol). Silica gel (3.5 kg, 1.8 wt. eq.) of silica gel was added to the organic phase, which was stirred overnight. Deloxan THP II metal scavenger (358 g) and heptane (17.6 L) were added and the resulting mixture was stirred for NLT 3 h. The mixture was filtered through a sintered glass funnel. The filter cake was washed with 30% ethyl acetate in heptane (25 L). The combined filtrates were concentrated under reduced pressure to give N-benzylglycolated-5-amino-2-(2-benzyloxy-1,1-dimethylethyl)-6-fluoroindole as a brown paste (1.4 kg).

Synthesis of Compound 1

Synthesis of Benzyl Protected Compound 1

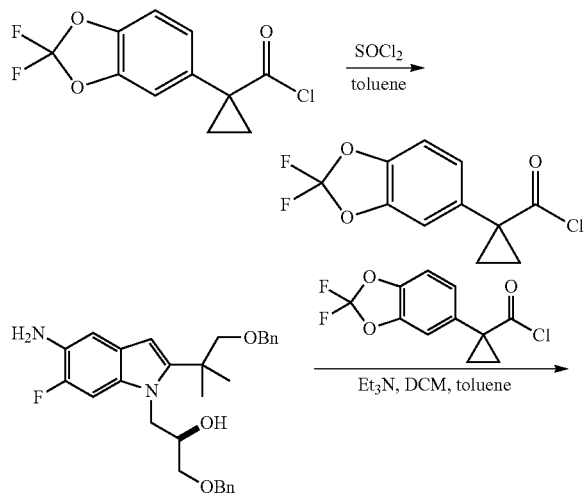

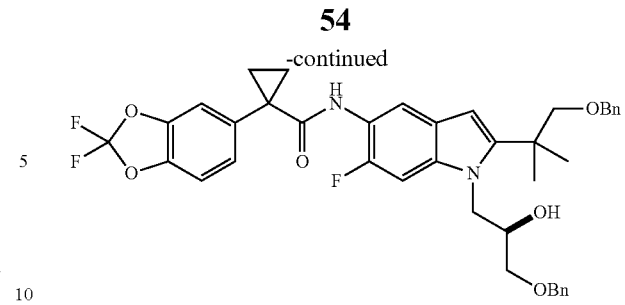

1-(2,2-Difluoro-1,3-benzodioxol-5-yl)-cyclopropanecarboxylic acid (1.3 equiv) was slurried in toluene (2.5 vol, based on 1-(2,2-difluoro-1,3-benzodioxol-5-yl)-cyclopropanecarboxylic acid). Thionyl chloride (SOCl$_2$, 1.7 equiv) was added via addition funnel and the mixture was heated to 60° C. The resulting mixture was stirred for 2 h. The toluene and the excess SOCl2 were distilled off using rotavop. Additional toluene (2.5 vol, based on 1-(2,2-difluoro-1,3-benzodioxol-5-yl)-cyclopropanecarboxylic acid) was added and the mixture was distilled down to 1 vol of toluene. A solution of (R)-1-(5-amino-2-(1-(benzyloxy)-2-methylpropan-2-yl)-6-fluoro-1H-indol-1-yl)-3-(benzyloxy)propan-2-ol (1 eq) and triethylamine (3 eq) in DCM (4 vol) is cooled to 0° C. The acid chloride solution in toluene (1 vol) is added while maintaining the batch temperature below 10° C. The reaction progress is monitored by HPLC, and the reaction is usually complete within minutes. After warming to 25° C., the reaction mixture is washed with 5% NaHCO$_3$ (3.5 vol), 1 M NaOH (3.5 vol) and 1 M HCl (5 vol). A solvent swap to into methanol (2 vol) is performed and the resulting solution of (R)—N-(1-(3-(benzyloxy)-2-hydroxypropyl)-2-(1-(benzyloxy)-2-methylpropan-2-yl)-6-fluoro-1H-indol-5-yl)-1-(2,2-difluorobenzo[d][1,3]dioxol-5-yl)cyclopropanecarboxamide in methanol is used without further manipulation in the next step (hydrogenolysis).

Synthesis of Compound 1

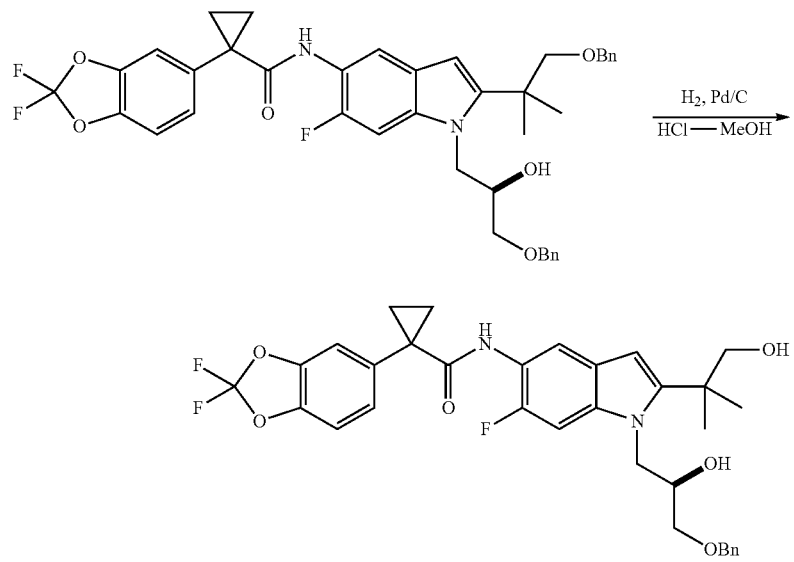

Compound 1

5% palladium on charcoal (~50% wet, 0.01 eq) is charged to an appropriate hydrogenation vessel. The (R)—N-(1-(3-(benzyloxy)-2-hydroxypropyl)-2-(1-(benzyloxy)-2-methylpropan-2-yl)-6-fluoro-1H-indol-5-yl)-1-(2,2-difluorobenzo[d][1,3]dioxol-5-yl)cyclopropanecarboxamide solution in methanol (2 vol) obtained above is added carefully, followed by a 3 M solution of HCl in methanol. The vessel is purged with nitrogen gas and then with hydrogen gas. The mixture is stirred vigorously until the reaction is complete, as determined by HPLC analysis. Typical reaction time is 3-5 h. The reaction mixture is filtered through Celite and the cake is washed with methanol (2 vol). A solvent swap into isopropanol (3 vol) is performed. Crude VX-661 is crystallized from 75% IPA-heptane (4 vol, ie. 1 vol heptane added to the 3 vol of IPA) and the resulting crystals are matured in 50% IPA-heptane (i.e. 2 vol of heptane added to the mixture). Typical yields of compound 4 from the two-step acylation/hydrogenolysis procedure range from 68% to 84%. Compound 4 can be recrystallized from IPA-heptane following the same procedure just described.

Compound 1 may also be prepared by one of several synthetic routes disclosed in US published patent application US20090131492, incorporated herein by reference.

Table 10 below recites analytical data for Compound 1.

TABLE 10

| Cmpd. No. | LC/MS M + 1 | LC/RT min | NMR |
|---|---|---|---|
| 1 | 521.5 | 1.69 | 1H NMR (400.0 MHz, CD$_3$CN) d 7.69 (d, J = 7.7 Hz, 1H), 7.44 (d, J = 1.6 Hz, 1H), 7.39 (dd, J = 1.7, 8.3 Hz, 1H), 7.31 (s, 1H), 7.27 (d, J = 8.3 Hz, 1H), 7.20 (d, J = 12.0 Hz, 1H), 6.34 (s, 1H), 4.32 (d, J = 6.8 Hz, 2H), 4.15-4.09 (m, 1H), 3.89 (dd, J = 6.0, 11.5 Hz, 1H), 3.63-3.52 (m, 3H), 3.42 (d, J = 4.6 Hz, 1H), 3.21 (dd, J = 6.2, 7.2 Hz, 1H), 3.04 (t, J = 5.8 Hz, 1H), 1.59 (dd, J = 3.8, 6.8 Hz, 2H), 1.44 (s, 3H), 1.33 (s, 3H) and 1.18 (dd, J = 3.7, 6.8 Hz, 2H) ppm. |

Assays

Assays for Detecting and Measuring ΔF508-CFTR Correction Properties of Compounds Membrane Potential Optical Methods for Assaying ΔF508-CFTR Modulation Properties of Compounds The optical membrane potential assay utilized voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential (V$_m$) cause the negatively charged DiSBAC$_2$(3) to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

1. Identification of Correction Compounds

To identify small molecules that correct the trafficking defect associated with ΔF508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ΔF508-CFTR. The cells were subsequently rinsed 3× with Krebs Ringers solution and loaded with the voltage-sensitive dyes. To activate ΔF508-CFTR, 10 μM forskolin and the CFTR potentiator, genistein (20 PM), were added along with Cl$^-$-free medium to each well. The addition of Cl$^-$-free medium promoted Cl$^-$ efflux in response to ΔF508-CFTR activation and the resulting membrane depolarization was optically monitored using the FRET-based voltage-sensor dyes.

2. Identification of Potentiator Compounds

To identify potentiators of ΔF508-CFTR, a double-addition HTS assay format was developed. During the first addition, a Cl$^-$ free medium with or without test compound was added to each well. After 22 sec, a second addition of Cl$^-$-free medium containing 2-10 μM forskolin was added to activate ΔF508-CFTR. The extracellular Cl$^-$ concentration following both additions was 28 mM, which promoted Cl$^-$ efflux in response to ΔF508-CFTR activation and the resulting membrane depolarization was optically monitored using the FRET-based voltage-sensor dyes.

3. Solutions

Bath Solution #1: (in mM) NaCl 160, KCl 4.5, CaCl$_2$ 2, MgCl$_2$ 1, HEPES 10, pH 7.4 with NaOH.

Chloride-free bath solution: Chloride salts in Bath Solution #1 are substituted with gluconate salts.

CC2-DMPE: Prepared as a 10 mM stock solution in DMSO and stored at −20° C.

DiSBAC$_2$(3): Prepared as a 10 mM stock in DMSO and stored at −20° C.

4. Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, 13-ME, 1× pen/strep, and 25 mM HEPES in 175 cm$^2$ culture flasks. For all optical assays, the cells were seeded at 30,000/well in 384-well matrigel-coated plates and cultured for 2 hrs at 37° C. before culturing at 27° C. for 24 hrs for the potentiator assay. For the correction assays, the cells are cultured at 27° C. or 37° C. with and without compounds for 16-24 hours.

Electrophysiological Assays for Assaying ΔF508-CFTR Modulation Properties of Compounds 1. Ussing Chamber Assay Using chamber experiments were performed on polarized epithelial cells expressing ΔF508-CFTR to further characterize the ΔF508-CFTR modulators identified in the optical assays. FRT$^{\Delta F508\text{-}CFTR}$ epithelial cells grown on Costar Snapwell cell culture inserts were mounted in an Ussing chamber (Physiologic Instruments, Inc., San Diego, Calif.), and the monolayers were continuously short-circuited using a Voltage-clamp System (Department of Bioengineering, University of Iowa, IA, and, Physiologic Instruments, Inc., San Diego, Calif.). Transepithelial resistance was measured by applying a 2-mV pulse. Under these conditions, the FRT epithelia demonstrated resistances of 4 KΩ/cm$^2$ or more. The solutions were maintained at 27° C. and bubbled with air. The electrode offset potential and fluid resistance were corrected using a cell-free insert. Under these conditions, the current reflects the flow of Cl$^-$ through ΔF508-CFTR expressed in the apical membrane. The $I_{SC}$ was digitally acquired using an MP100A-CE interface and AcqKnowledge software (v3.2.6; BIOPAC Systems, Santa Barbara, Calif.).

2. Identification of Correction Compounds

Typical protocol utilized a basolateral to apical membrane Cl$^-$ concentration gradient. To set up this gradient, normal ringer was used on the basolateral membrane, whereas apical NaCl was replaced by equimolar sodium gluconate (titrated to pH 7.4 with NaOH) to give a large Cl$^-$ concentration gradient across the epithelium. All experiments were performed with intact monolayers. To fully activate ΔF508-CFTR, forskolin (10 μM) and the PDE inhibitor, IBMX (100 μM), were applied followed by the addition of the CFTR potentiator, genistein (50 μM).

As observed in other cell types, incubation at low temperatures of FRT cells stably expressing ΔF508-CFTR increases the functional density of CFTR in the plasma membrane. To determine the activity of correction compounds, the cells were incubated with 10 μM of the test compound for 24 hours at 37° C. and were subsequently washed 3× prior to recording. The cAMP- and genistein-mediated $I_{SC}$ in compound-treated cells was normalized to the 27° C. and 37° C. controls and expressed as percentage activity. Preincubation of the cells with the correction compound significantly increased the cAMP- and genistein-mediated $I_{SC}$ compared to the 37° C. controls.

3. Identification of Potentiator Compounds

Typical protocol utilized a basolateral to apical membrane Cl$^-$ concentration gradient. To set up this gradient, normal ringers was used on the basolateral membrane and was permeabilized with nystatin (360 μg/ml), whereas apical NaCl was replaced by equimolar sodium gluconate (titrated to pH 7.4 with NaOH) to give a large Cl$^-$ concentration gradient across the epithelium. All experiments were performed 30 min after nystatin permeabilization. Forskolin (10 μM) and all test compounds were added to both sides of the cell culture inserts. The efficacy of the putative ΔF508-CFTR potentiators was compared to that of the known potentiator, genistein.

4. Solutions

Basolateral solution (in mM): NaCl (135), CaCl$_2$ (1.2), MgCl$_2$ (1.2), K$_2$HPO$_4$ (2.4), KHPO$_4$ (0.6), N$^2$-hydroxyethylpiperazine-N'-2-ethanesulfonic acid (HEPES) (10), and dextrose (10). The solution was titrated to pH 7.4 with NaOH.

Apical solution (in mM): Same as basolateral solution with NaCl replaced with Na Gluconate (135).

5. Cell Culture

Fisher rat epithelial (FRT) cells expressing ΔF508-CFTR (FRT$^{\Delta F508\text{-}CFTR}$) were used for Ussing chamber experiments for the putative ΔF508-CFTR modulators identified from our optical assays. The cells were cultured on Costar Snapwell cell culture inserts and cultured for five days at 37° C. and 5% CO$_2$ in Coon's modified Ham's F-12 medium supplemented with 5% fetal calf serum, 100 U/ml penicillin, and 100 μg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

6. Whole-cell Recordings

The macroscopic ΔF508-CFTR current ($I_{\Delta F508}$) in temperature- and test compound-corrected NIH3T3 cells stably expressing ΔF508-CFTR were monitored using the perforated-patch, whole-cell recording. Briefly, voltage-clamp recordings of $I_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl$^-$ ($E_{Cl}$) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 μl of saline and was continuously perifused at a rate of 2 ml/min using a gravity-driven perfusion system.

7. Identification of Correction Compounds

To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 μM forskolin and 20 μM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 μM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 μM of correction compounds significantly increased the cAMP- and genistein-dependent current compared to the 37° C. controls.

8. Identification of Potentiator Compounds

The ability of ΔF508-CFTR potentiators to increase the macroscopic ΔF508-CFTR Cl$^-$ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

9. Solutions

Intracellular solution (in mM): Cs-aspartate (90), CsCl (50), MgCl$_2$ (1), HEPES (10), and 240 μg/ml amphotericin-B (pH adjusted to 7.35 with CsOH).

Extracellular solution (in mM): N-methyl-D-glucamine (NMDG)-Cl (150), MgCl$_2$ (2), CaCl$_2$ (2), HEPES (10) (pH adjusted to 7.35 with HCl).

10. Cell Culture

NIH3T3 mouse fibroblasts stably expressing ΔF508-CFTR are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

11. Single-channel Recordings

The single-channel actdivities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1-2 sec. To maintain ΔF508-CFTR activity during the rapid perifusion, the non-specific phosphatase inhibitor $F^-$ (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing ≤2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o = I/i(N)$, where I=mean current, i=single–channel current amplitude, and N=number of active channels in patch.

12. Solutions

Extracellular solution (in mM): NMDG (150), aspartic acid (150), $CaCl_2$ (5), $MgCl_2$ (2), and HEPES (10) (pH adjusted to 7.35 with Tris base).

Intracellular solution (in mM): NMDG-Cl (150), $MgCl_2$ (2), EGTA (5), TES (10), and Tris base (14) (pH adjusted to 7.35 with HCl).

3. Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

Using the procedures described above, the activity, i.e., EC50s, of Compound 1 has been measured and is shown in Table 11.

TABLE 11

| EC50 Bins: +++ <= 2.0 < ++ <= 5.0 < + | | |
|---|---|---|
| PercentActivity Bins. + <= 25.0 < ++ <= 100.0 < +++ | | |
| Cmpd. No. | Binned EC50 | Binned MaxEfficacy |
| 1 | +++ | +++ |

We claim:

1. A method for preparing a compound of formula IV:

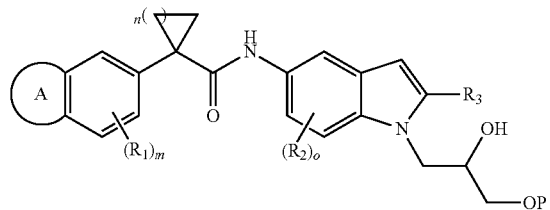

wherein, independently for each occurrence:
  ring A is a fused cycloalkyl, heterocycloalkyl, aryl, or heteroaryl ring;
  $R_1$ and $R_2$ is independently selected from $-R^J$, $-OR^J$, $-N(R^J)_2$, $-NO_2$, halogen, $-CN$, $-C_{1-4}$haloalkyl, $-C_{1-4}$haloalkoxy, $-C(O)N(R^J)_2$, $-NR^JC(O)R^J$, $-SOR^J$, $-SO_2R^J$, $-SO_2N(R^J)_2$, $-NR^JSO_2R^J$, $-COR^J$, $-CO_2R^J$, $-NR^JSO_2N(R^J)_2$, $-COCOR^J$;
  $R^J$ is hydrogen or $C_{1-6}$ aliphatic;
  $R_3$ is $C_{1-6}$ aliphatic optionally substituted with OH, OP, $-O-C_{1-6}$ aliphatic, aryl, heteroaryl, $-O$-aryl, or $-O$-heteroaryl;
  P is a protecting group;
  m is an integer from 0 to 3 inclusive;
  n is an integer from 1 to 4 inclusive; and
  o is an integer from 1 to 3 inclusive;
comprising the steps of:
  a) reacting a compound of formula IIIA:

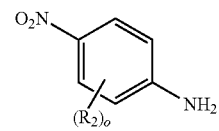

wherein, independently for each occurrence:
  $R_2$ is $-R^J$, $-OR^J$, $-N(R^J)_2$, $-NO_2$, halogen, $-CN$, $-C_{1-4}$haloalkyl, $-C_{1-4}$haloalkoxy, $-C(O)N(R^J)_2$, $-NR^JC(O)R^J$, $-SOR^J$, $-SO_2R^J$, $-SO_2N(R^J)_2$, $-NR^JSO_2R^J$, $-COR^J$, $-CO_2R^J$, $-NR^JSO_2N(R^J)_2$, $-COCOR^J$;
  $R^J$ is hydrogen or $C_{1-6}$ aliphatic; and
  o is an integer from 0 to 3;
with a halogenating reagent in a first organic solvent to form a compound of formula IIIB:

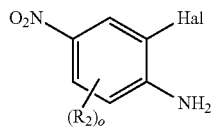

IIIB wherein, independently for each occurrence:

R$_2$ is —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;

R$^J$ is hydrogen or C$_{1-6}$ aliphatic;

o is an integer from 0 to 3; and

Hal is a halide;

b) reacting the compound of formula IIIB in a second organic solvent with a compound of formula IIIC:

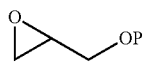

IIIC wherein:

P is a protecting group;

followed by reduction and treatment with acid to form a compound of formula IIID:

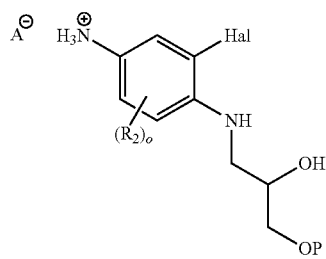

IIID wherein:

R$_2$ is —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;

R$^J$ is hydrogen or C$_{1-6}$ aliphatic;

o is an integer from 0 to 3;

Hal is a halide;

P is a protecting group; and

A$^\ominus$ is an anion;

c) neutralizing a compound of formula IIID in the presence of a base to form a compound of formula IIID-a:

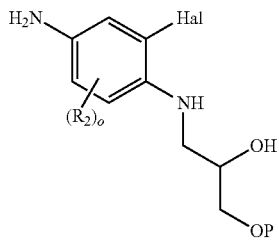

IIID-a wherein:

R$_2$ is —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;

R$^J$ is hydrogen or C$_{1-6}$ aliphatic;

o is an integer from 0 to 3;

Hal is a halide; and

P is a protecting group;

d reacting a compound of formula IIID in a third organic solvent with a compound of formula IIIE:

IIIE wherein, independently for each occurrence:

R$_3$ is a C$_{1-6}$ aliphatic optionally substituted with OH, OP, —O—C$_{1-6}$ aliphatic, aryl, heteroaryl, —O-aryl, or —O-heteroaryl;

in the presence of a catalyst to form a compound of formula III:

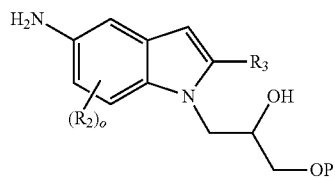

III wherein, independently for each occurrence:

R$_2$ is —R$^J$, —OR$^J$, —N(R$^J$)$_2$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SOR$^J$, —SO$_2$R$^J$, —SO$_2$N(R$^J$)$_2$, —NR$^J$SO$_2$R$^J$, —COR$^J$, —CO$_2$R$^J$, —NR$^J$SO$_2$N(R$^J$)$_2$, —COCOR$^J$;

R$^J$ is hydrogen or C$_{1-6}$ aliphatic;

R$_3$ is C$_{1-6}$ aliphatic optionally substituted with OH, OP, —O—C$_{1-6}$ aliphatic, aryl, heteroaryl, —O—aryl, or —O-heteroaryl;

P is a protecting group; and o is an integer from 0 to 3;

e reacting the compound of formula III in a fourth organic solvent with a compound of formula II:

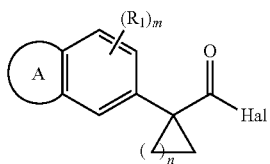

II wherein, independently for each occurrence:
ring A is a fused cycloalkyl, heterocycloalkyl, aryl, or heteroaryl ring;
Hal is a halide;
$R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
$R^J$ is hydrogen or $C_{1-6}$ aliphatic;
m is an integer from 0 to 3 inclusive; and
n is an integer from 1 to 4 inclusive;
to form the compound of formula IV.

2. The method of claim 1, wherein in formula IV, ring A is

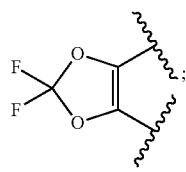

o is 1 and $R_2$ is F; P is benzyl; and $R_3$ is a $C_4$ aliphatic optionally substituted with OP.

3. The method of claim 1, wherein in formula IV, $R_3$ is

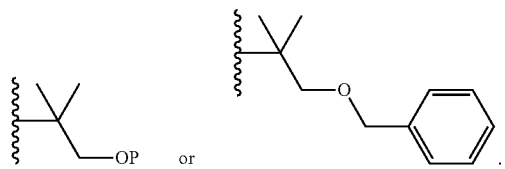

4. The method of claim 1, wherein in formula IV, ring A is

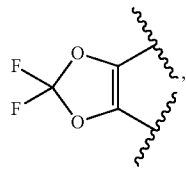

m is 0, n is 1, o is 1 and $R_2$ is F, P is benzyl, and $R_3$ is

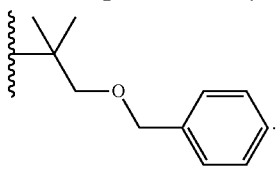

5. The method of claim 1, wherein step a) takes place at about 2 ° C. to 42 ° C., the halogenating reagent is N-bromosuccinimide, and the first organic solvent is an aprotic solvent.

6. The method of claim 1, wherein in step a), the first organic solvent is ethyl acetate.

7. The method of claim 1, wherein in formula IIIB, o is 1, $R_2$ is F, and Hal is Br.

8. The method of claim 1, wherein in formula IIIC, P is benzyl.

9. The method of claim 1, wherein in step b), the reaction with a compound of formula IIIC takes place at about 60 ° C. to 100 ° C. , the acid is p-toluenesulfonic acid, the reduction is carried out with hydrogen , and the second organic solvent is an aprotic solvent.

10. The method of claim 1, wherein in step b), the second organic solvent is toluene.

11. The method of claim 1, wherein in formula IIID, o is 1, $R_2$ is F, Hal is Br, $A^{\ominus}$ is Tos$^-$, and P is benzyl.

12. The method of claim 1, wherein in formula IIIE, $R_3$ is $C(CH_3)_2CH_2O$(benzyl).

13. The method of claim 1, wherein in step c), the base is an inorganic base.

14. The method of claim 1, wherein step d takes place at about 60° C. to 100° C., the catalyst is a palladium catalyst , and the third organic solvent is an aprotic solvent.

15. The method of claim 1, wherein in step d, the third organic solvent is acetonitrile.

16. The method of claim 1, wherein in step d, the catalyst is selected from palladium(II)acetate, Pd(dppf)Cl$_2$, Pd(dba)$_2$, tetrakis(triphenylphosphine)palladium(0), (MeCN)$_2$PdCl$_2$, or tris(dibenzylideneacetone)dipalladium(0).

17. The method of claim 1, wherein in step d, the catalyst is palladium(II)acetate.

18. The method of claim 1 wherein in step e, ring A is

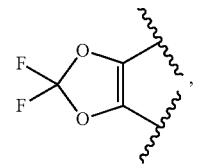

m is 0, n is 1, and Hal is Cl.

19. The method of claim 1, wherein in step e, the fourth organic solvent is an aprotic solvent.

20. The method of claim 1, wherein step e takes place at about −20° C. to 20° C., the compound of formula II is prepared in situ by halogenating the acid precursor and reacted with the compound of formula III without isolation, and the fourth organic solvent is dichloromethane.

21. The method of claim 1, further comprising removing the two protecting groups from the compound of formula IV to form a compound of formula IVA:

IVA

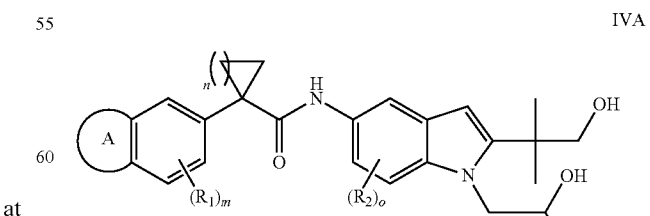

22. The method of claim 21, wherein the protecting groups are removed by hydrogenation.

23. A method of preparing Compound 1:

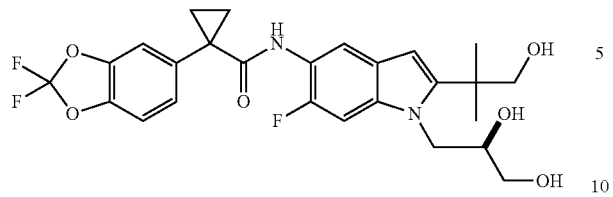

comprising the steps of:
a) reacting compound 2:

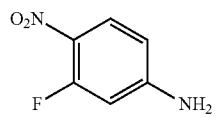

with a brominating reagent to form a compound 3:

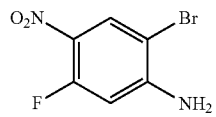

b) reacting compound 3 with compound 4:

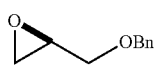

followed by reduction to form compound 5:

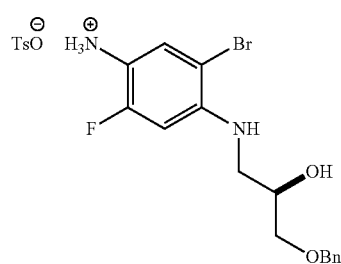

followed by neutralizing compound 5 with a base to give compound 5a:

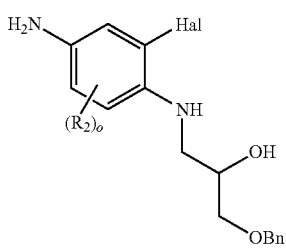

c) reacting compound 5a with compound 6:

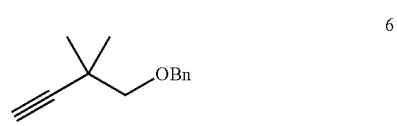

in the presence of a catalyst to form compound 7:

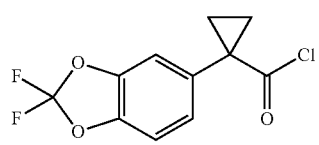

d) reacting compound 7 with compound 8:

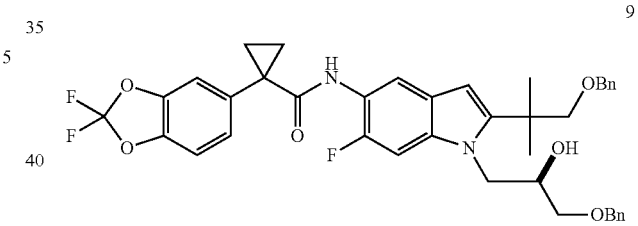

to form compound 9:

and
e) removing the two Bn protecting groups to form Compound 1.

24. The method of claim 23, wherein:
in step a), the brominating agent is N-bromosuccinimide;
in step b), the reduction is carried out with hydrogen;
in step c), the catalyst is a palladium catalyst;
in step d), compound 8 is made in situ by halogenating the acid precursor without isolation; and
in step e), the Bn protecting groups are removed by hydrogenation.

25. The method of claim 23, wherein in step c), the catalyst is selected from palladium(II)acetate, Pd(dppf)Cl$_2$, Pd(dba)$_2$, tetrakis(triphenylphosphine)palladium(0), (MeCN)$_2$PdCl$_2$, or tris(dibenzylideneacetone)dipalladium(0).

26. The method of claim 23, wherein in step c), the catalyst is palladium(II)acetate.

* * * * *